US011456079B2

(12) United States Patent  
Barrett et al.

(10) Patent No.: US 11,456,079 B2  
(45) Date of Patent: Sep. 27, 2022

(54) IDENTIFICATION OF ASTHMA TRIGGERING CONDITIONS BASED ON MEDICAMENT DEVICE MONITORING FOR A PATIENT

(71) Applicant: Reciprocal Labs Corporation, Madison, WI (US)

(72) Inventors: Meredith A. Barrett, Redwood City, CA (US); Robert Austin Lee, San Francisco, CA (US); John David Van Sickle, Oregon, WI (US); Christopher Hogg, San Francisco, CA (US); Michael Lohmeier, Sun Prairie, WI (US); Lucas Karl Dailey, Madison, WI (US); Mark William Sehmer, Stoughton, WI (US); Ki Hong Han, Dublin, CA (US); Ian Daniel Alderman, Fitchburg, WI (US)

(73) Assignee: Reciprocal Labs Corporation, Madison, WI (US)

( * ) Notice: Subject to any disclaimer, the term of this patent is extended or adjusted under 35 U.S.C. 154(b) by 0 days.

(21) Appl. No.: 16/104,092

(22) Filed: Aug. 16, 2018

(65) Prior Publication Data

US 2020/0058403 A1 Feb. 20, 2020

(51) Int. Cl.
*G16H 50/30* (2018.01)
*G16H 10/60* (2018.01)

(52) U.S. Cl.
CPC .............. *G16H 50/30* (2018.01); *G16H 10/60* (2018.01)

(58) Field of Classification Search
CPC ................................ G16H 50/30; G16H 10/60

USPC .............................................................. 705/3
See application file for complete search history.

(56) References Cited

U.S. PATENT DOCUMENTS 9,550,031 B2 * 1/2017 Tracy ..................... G16H 40/67  
2002/0186137 A1 12/2002 Skardon  
(Continued)

FOREIGN PATENT DOCUMENTS

EP            1936522 A1 * 6/2008 ............. G16H 50/30  
WO    WO-2014071145 A1 * 5/2014 ............. G16H 50/30

OTHER PUBLICATIONS

Karthikeyan, R., Krishnamoorthy, S., Maamidi, S., Kaza, A. M., & Balasubramanian, N. (2014). Effect of inhaled corticosteroids on systemic inflammation in asthma. Perspectives in clinical research, 5(2), 75. (Year: 2014).*

(Continued)

*Primary Examiner* — Joshua B Blanchette  
*Assistant Examiner* — Winston Furtado  
(74) *Attorney, Agent, or Firm* — Fenwick & West LLP

(57) ABSTRACT

This description provides trigger identification notifications to patients suffering from respiratory diseases based on large amounts of patient data in order to help effect behavior changes in a patient to prevent inhaler rescue usage events from occurring. Rescue medication events, environmental conditions, and other contextually relevant patient information are detected by sensors associated with the patient's medicament devices and are collected from other sources, respectively to provide a basis to determine identify various triggers of rescue inhaler usage events for a patient. Each trigger is analyzed to determine the severity of the patient's reaction to the trigger and is used to send notifications accordingly.

23 Claims, 13 Drawing Sheets

(56) References Cited

U.S. PATENT DOCUMENTS

| 2015/0150484 | A1  | 6/2015  | Wekell        |            |
|--------------|-----|---------|---------------|------------|
| 2015/0174348 | A1  | 6/2015  | Tunnell et al.|            |
| 2015/0254330 | A1* | 9/2015  | Chan          | G06F 16/219 |
|              |     |         |               | 707/613    |
| 2016/0055307 | A1* | 2/2016  | Macoviak      | G16H 10/60 |
|              |     |         |               | 705/2      |
| 2016/0314256 | A1* | 10/2016 | Su            | G16H 50/50 |
| 2017/0109493 | A1* | 4/2017  | Hogg          | G16H 10/60 |

OTHER PUBLICATIONS

Krieger, J. W., Takaro, T. K., Song, L., & Weaver, M. (2005). The Seattle-King County Healthy Homes Project: a randomized, controlled trial of a community health worker intervention to decrease exposure to indoor asthma triggers. American journal of public health, 95(4), 652-659. (Year: 2005).*

Tsai, C. L., Clark, S., Sullivan, A. F., & Camargo, Jr, C. A. (2009). Development and Validation of a Risk-Adjustment Tool in Acute Asthma. Health services research, 44(5p1), 1701-1717. (Year: 2009).*

Vink, N. M., Postma, D. S., Schouten, J. P., Rosmalen, J. G., & Boezen, H. M. (2010). Gender differences in asthma development and remission during transition through puberty: the TRacking Adolescents' Individual Lives Survey (TRAILS) study. Journal of allergy and clinical immunology, 126(3), 498-504. (Year: 2010).*

Tang, M., Agrawal, P., & Jain, R. (Jun. 2015). Habits vs environment: What really causes asthma?. In Proceedings of the ACM Web Science Conference (pp. 1-5) (Year: 2015).*

PCT International Search Report and Written Opinion, PCT Application No. PCT/US19/46404, dated Oct. 29, 2019, 15 pages.

* cited by examiner

Process for Identifying Trigger Conditions
600

*Process for Clustering Module*
530

| Patient | Relative Weight | Date | Rescue Event? | Med. Amount | Adherence | Gender | Age | Home Location | Temperature | Humidity | Station Pressure | Wind Speed | NO2 | O3 | SO2 | PM2.5 | PM10 |
|---|---|---|---|---|---|---|---|---|---|---|---|---|---|---|---|---|---|
| 1 | 1.0 | May 25 | 1 | 1 | 1 | 1 | 1 | 1 | 1 | 0 | 1 | 1 | 1 | 0 | 1 | 1 | 1 |
| 2.a | .9 | May 25 | 1 | 1 | 1 | 1 | 1 | 1 | 1 | 0 | 1 | 1 | 1 | 1 | 1 | 1 | 1 |
| 2.b | .7 | May 25 | 1 | 1 | 0 | 1 | 0 | 1 | 1 | 0 | 0 | 0 | 0 | 0 | 1 | 0 | 0 |
| 2.c | .4 | May 25 | 0 | 0 | 1 | 1 | 1 | 0 | 0 | 1 | 0 | 0 | 0 | 1 | 0 | 0 | 0 |
| 2.d | .1 | May 25 | 0 | 0 | 0 | 0 | 0 | 0 | 0 | 1 | 0 | 0 | 0 | 1 | 0 | 0 | 0 |

Trigger Conditions: Date, Rescue Event?, < 2 puffs?, < 2x a day, Male?, >35, < 10 miles, > 85°F, > 70%, < 40 mb, > 10 mph, > 80%, > 23%, > 8%, < 10 μg/m³, > 2 μg/m³

*Example Aggregate Dataset 900*

*FIG. 9*

IDENTIFICATION OF ASTHMA TRIGGERING CONDITIONS BASED ON MEDICAMENT DEVICE MONITORING FOR A PATIENT

BACKGROUND

Field of Art

The disclosure relates generally to methods of improving treatment for patients who use inhalers, and more specifically to determining a patient's causes of asthma-related rescue events.

Description of the Related Art

Asthma remains a significant and costly public health problem. In the United States, more than 22 million people have the disease. Worldwide, the World Health Organization estimates the population with asthma may be 300 million, and predicts that it will rise to 400 million by 2025.

Despite the development of new medications, rates of hospitalizations and emergency room visits have not declined. Each year in the United States the disease causes approximately 2 million emergency department visits, 500,000 hospitalizations, and 5,000 deaths. In addition, asthma is responsible for an estimated 15 million missed days of school, and 12 million days of work. Total annual costs to US health insurers and employers are greater than $18 billion.

The majority of these exacerbations could be prevented with currently available treatments, however, only 1 in 5 asthmatics has the disease under control. Newly revised national guidelines urge doctors to more closely monitor whether treatment is controlling everyday symptoms and improving quality of life. An increasing number of physicians have begun to use periodic, written questionnaires (such as the Asthma Control Test) to monitor patients and their conditions. These instruments require patients to accurately recall and report the symptoms, frequency of symptoms, inhaler usage, and activity level and restriction over some period of time (usually two to four weeks). As a result, these questionnaires are subject to error introduced by biases (recall), different interpretations of symptoms, and behaviors (non-adherence), and only provide information at the time they are used.

SUMMARY

Generally, medicament devices such as inhalers allow patients to manage respiratory symptoms. Many respiratory disease patients, such as sufferers of asthma, COPD, and cystic fibrosis, have symptoms that are related to environmental triggers and factors such as air quality, weather, land use, and the like. A patient being aware of which environmental triggers and factors affect their symptoms allows the patient to better manage their symptoms and reduce the chances for needing emergency medical care. However, a particular patient or group of patients may have sensitivities to multiple triggers and factors. Knowing which of dozens, hundreds, or more triggers and factors a patient is sensitive to and monitoring those triggers and factors for use in managing symptoms is a complex task and not a reasonable task for many patients and providers to perform manually.

To address this, an asthma analytics system is described that is a unified platform for treating, monitoring, and managing rescue events resulting from asthma. The asthma analytics system tracks asthma rescue medication events by receiving event notifications from a sensor attached to a medicament device (e.g., inhaler) used by a patient who has authorized the asthma analytics system to help manage their asthma. The sensor, when attached to or incorporated in a metered dose inhaler or other medicament device, records the geographical location, time, and date of the rescue usage event, and communicates that information to the asthma analytics system. The asthma analytics system analyzes the received events (both the most recent and previously received events) and over time identifies triggers responsible for causing a patient's rescue usage events and information to guide and manage the triggers in the form of a notification to patients and the healthcare providers.

Triggers are identified using a combination of various potential triggers (also referred to as features), examples of which may include several types of triggers such as information based on a patient's medical history, a historical record of the patient's use of the rescue inhaler unit, the patient's current contextual data, and environmental conditions relating to atmospheric and weather conditions. The relations between these features and trigger identification is embodied in a system implementing a machine learned model and a statistical analysis model. The system is capable of receiving input trigger values for each potential trigger to provide a trigger identification analysis with accurate and medically relevant recommendations to mitigate the risk posed by the trigger.

By ingesting information about the timing, frequency, and location of the usage of the medication along with other contextually relevant feature information, the asthma analytics system helps prevent the occurrence of future asthma rescue usage events by suggesting applicable changes in behavior or environment in advance of any identified triggers. This facilitates better management of an asthma treatment by the patient and their health care provider, and improve recognition of specific locations that precipitate rescue events so that the patient may avoid or accommodate these locations in the future.

BRIEF DESCRIPTION OF DRAWINGS

FIG. 9 is a diagram illustrating an exemplary aggregate dataset, according to one embodiment.

The figures depict various embodiments of the presented invention for purposes of illustration only. One skilled in the art will readily recognize from the following discussion that alternative embodiments of the structures and methods illustrated herein may be employed without departing from the principles described herein.

DETAILED DESCRIPTION

I. System Environment

Figure 1:
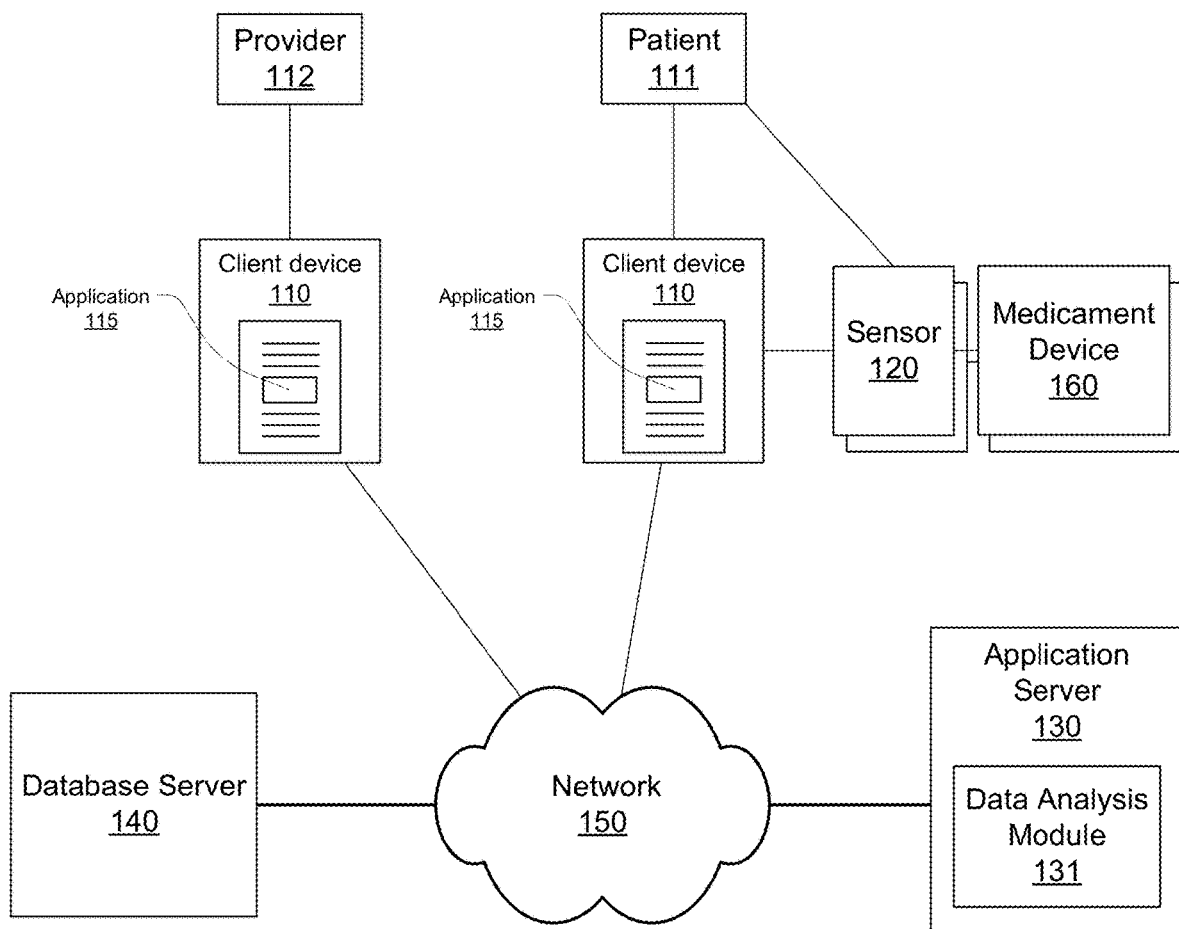
FIG. 1 shows an asthma analytics system for monitoring accurate, real-time medicament device usage, performing analytics on that data, and providing asthma rescue event risk notifications, according to one embodiment.

FIG. 1 shows an asthma analytics system 100 for monitoring accurate, real-time medicament device events, performing analytics on that data, and providing asthma rescue event risk notifications, according to one embodiment.

The asthma analytics system includes client computing devices 110, a medicament device sensor 120, a medicament device 160, an application server 130, database server 140, and a network 150. Although FIG. 1 illustrates only a single instance of most of the components of the asthma analytics system 100, in practice more than one of each component may be present, and additional or fewer components may be used.

I.A. Client Device and Application

The client devices 110, at the behest of their users, interact with the asthma analytics system 100 via the network 150. For purposes of explanation and clarity it is useful to identify at least two different types of users. A patient 111 is a user burdened with asthma who makes use of the asthma analytics system 100 at least in part to obtain personalized asthma rescue event risk notifications provided by the server 130 and asthma management notifications created by their health care provider 112. Such notifications can be provided in exchange for the user's permission to allow the asthma analytics system 100 to monitor the patient's 111 medicament device 160 usage. As will be explained below, medication events are detected by a sensor 120 associated with the medicament device 160 and the user's client device 100, which in turn reports to the application server 130, which in turn can initiate a process to generate risk notifications which are provided to the user through the client device 110.

Another type of user is a healthcare provider 112 who, again with the patient's 111 express permission, also receives notifications regarding a patient's asthma management, as well as aggregated asthma community rescue event data and derived statistics regarding asthma events and other associated data. Other types of users are also contemplated, such as parents/guardians of patients 111 who may also want to receive notifications in the event that their own client devices 110 are distinct from that of their children.

The client device 110 is a computer system. An example physical implementation is described more completely below with respect to FIG. 2. The client device 110 is configured to wirelessly communicate with the asthma analytics system 100 via network 150. With network 150 access, the client device 110 transmits to system 100 the user's geographical location and the time of a rescue medication event, as well as information describing the event as received from the associated medicament device sensor 120 (referred to throughout as "sensor 120").

Regarding user location and event times, the client device 110 may determine the geographical location and time of a rescue event through use of information about the cellular or wireless network 150 to which it is connected. For example, the current geographical location of the client device 110 may be determined by directly querying the software stack providing the network 150 connection. Alternatively, the geographical location information may be obtained by pinging an external web service (not shown in FIG. 1) made accessible via network 150. The time of an event can be provided by the sensor 120 as part of the event data or added to event data by querying an appropriate software routine available as part of the client device's native operating system.

In addition to communicating with the application server 130, client devices 110 connected wirelessly to the asthma analytics system 100 may also exchange information with other connected client devices 110. For example, through a client software application 115, a healthcare provider 112 may receive a risk exacerbation notification describing a recent rescue event about a patient 111, then in response send a recommendation to the patient 111 for post-asthma rescue event treatment. Similarly, through application 115 patients 111 may communicate with their health care providers 112 and other patients 111.

Application 115 provides a user interface (herein referred to as a "dashboard") that is displayed on a screen of the client device 110 and allows a user to input commands to control the operation of the application 115. The dashboard is the mechanism by which healthcare providers 112 and patients 111 access the COPD analytics system 100. For example, the dashboard allows patients 111 and providers 112 to interact with each other, receive asthma rescue event risk notifications, exchange messages about treatment, provide and receive additional event and non-event data, and so on. Application 115 may be coded as a web page, series of web pages, or content otherwise coded to render within an internet browser. Application 115 may also be coded as a proprietary application configured to operate on the native operating system of the client device 110. The dashboard is more completely described below in conjunction with FIG. 3.

In addition to providing the dashboard, application 115 may also perform some data processing on asthma rescue event data locally using the resources of client device 110 before sending the processed data through the network 150. Event data sent through the network 110 is received by the application server 130 where it is analyzed and processed for storage and retrieval in conjunction with database server 140. The application server 130 may direct retrieval and storage request to the database system 130 as required by the client application 115.

The client device 110 communicates with the sensor 120 using a network adapter and either a wired or wireless communication protocol, an example of which is the Bluetooth Low Energy (BTLE) protocol. BTLE is a short-ranged, low-powered, protocol standard that transmits data wirelessly over radio links in short range wireless networks. After the sensor 120 and client device 110 have been paired with each other using a BTLE passkey, the sensor 120 automatically synchronizes and communicate information relating to medicament device usage with the client device 110. If the sensor 120 hasn't been paired with a client device 110 prior to a rescue medication event, the information is stored locally until such a pairing occurs. Upon pairing, the sensor 120 communicates any stored event records to the client device 110. In other implementations, other types of wireless connections are used (e.g., infrared or 802.11).

Although client devices 110 and medicament devices 160 are described above as being separate physical devices (such as smart phones and inhalers, respectively), in the future it is contemplated the medicament devices 160 may include not only sensors 120 integrated into a single housing with the device 160, but also aspects of the client device 110. For example, a medicament device 160 may include an audiovisual interface including a display or other lighting elements as well as speakers for presenting visual audible information. In such an implementation the medicament device 160 itself may present the contents of notifications provided by the server 130 directly, in place of or in addition to presenting them through the client devices 110.

I.B. Medicament Device and Sensor

The medicament device 160 is a medical device used to deliver medication to the lungs of a user experiencing constricted respiratory airflow. Medicament devices (e.g. inhalers) are typically portable and small enough to be carried by hand for ease of accessibility when treating respiratory attacks. In one embodiment, medicine is delivered in aerosol form through a medicament device 160 such as a metered dose inhaler. Metered dose inhalers included a pressured propellant canister of aerosol medicine, a metering valve for delivering a regulated medicine dosage amount, and a plastic holder that holds the pressurized canister and also forms a mouthpiece for delivery of the medicine. In another embodiment, medicine is delivered in dry powder form through a medicament device 160 such as a dry powder inhaler. Dry powder inhalers may have Cartesian ovular shaped bodies that house wheel and gear mechanisms enabling a user to index through a strip of dry powder medication. The bodies of dry powder inhalers also include a manifold and a mouthpiece to deliver dry powder to the user. Examples of controller medications that are dispensed by a controller medicament device 160 include beclomethasone, budesonide, and fluticasone as well as combinations of those medications with a long-acting bronchodilator such as salmeterol or formoterol. Examples of rescue medications that are dispensed by a rescue medicament device 160 include albuterol, salbutamol, levalbuterol, metaproterenol, and terbutaline.

Each patient may be associated with more than one medicament device 160. For example, the patient may have a rescue medicament device 160 that dispenses rescue medication, and a controller medicament device 160 that dispenses controller medication. Similarly, each patient may be associated with more than one sensor 120, each chosen to operate with one of the patient's medicament devices 160.

Generally, a sensor 120 is a physical device that monitors the usage of the medicament dispenser 160. The sensor 120 is either removably attachable to the medicament dispenser without impeding the operation of the medication dispenser, or the sensor 120 is an integrated component that is a native part of the medicament dispenser 160 as made available by its manufacturer.

The sensor 120 includes its own network adapter (not shown) that communicates with the client device 110 either through a wired connection, or more typically through a wireless radio frequency connection. In one embodiment, the network adapter is a Bluetooth Low Energy (BTLE) wireless transmitter, however in other embodiments other types of wireless communication may be used (e.g., infrared, 802.11).

The sensor 120 may also be configured to communicate more directly with the application server 130. For example, if the network adapter of the sensor 120 is configured to communicate via a wireless standard such as 802.11 or LTE, the adapter may exchange data with a wireless access point such as a wireless router, which may in turn communicate with the application server 130 without necessarily involving the client device 110 in every exchange of data. These two methods of communicating are not mutually exclusive, and the sensor 120 may be configured to communicate with both the client device 110 and the application server 130, for example using redundant transmission to ensure event data arrives at the application server 130 or to provide information directly to the client device 110 while the application server 130 is determining what notification to provide in response to an event.

As introduced above, the sensor 120 captures data about usage of the medicament device 160. Specifically, each sensor 120 captures the time and geographical location of the rescue medication event, that is, usages of the rescue medicament device 160, by the patient 111. Each sensor 120 transmits the event data in real-time or as soon as a network connection is achieved, automatically without input from the patient 111 or health care provider 112. The medication event information is sent to the application server 130 for use in analysis, generation of asthma rescue event notifications, and in aggregate analyses of event data across multiple patients.

To accomplish this goal, there are a number of different ways for the sensor 120 to be constructed, and in part the construction will depend upon the construction of the medicament device itself 160. Generally, all sensors 120 will include an onboard processor, persistent memory, and the network adapter mentioned above that together function to record, store, and report medication event information to the client device 110 and/or server 130. Sensors 120 may also include a clock for recording the time and date of events.

Regarding specific sensor 120 constructions, traditional inhalers, such as mechanical dose counters, are not designed with sensors 120 in mind, and thus the sensor 120 may be constructed accordingly. Some implementations in this manner include mechanical, electrical, or optical sensors to detect movement of the device 160, priming of the device, activation of the device, inhalation by the user, etc. In contrast, modern inhalers, such as deflectable membrane dose counters, include electrical circuitry may report event information as an electrical data signal which a sensor 120 is designed to receive and interpret, for example the medicament device 160 itself may report movement, priming, and activation to the sensor 120.

More information regarding hardware and software components for the sensors 120 and medicament devices 160, as well as the interaction between them to record rescue medication events can be found in U.S. patent application Ser. No. 12/348,424, filed Jan. 1, 2009, and International Application No. PCT/US2014/039014, filed May 21, 2014, both of which are incorporated by reference herein in their entirety.

I.C. Application Server

Figure 2:
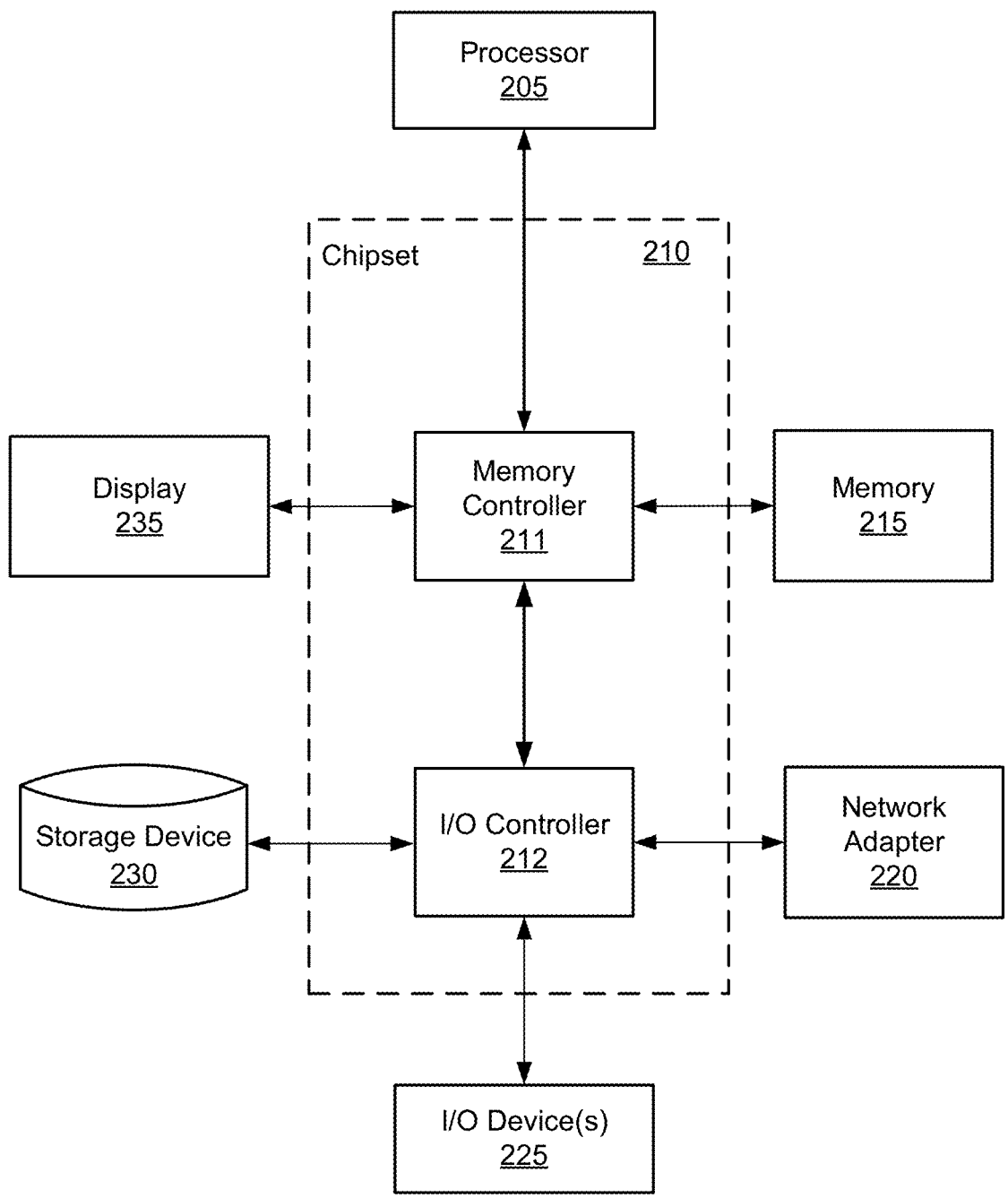
FIG. 2 is a high-level block diagram illustrating an example of a computing device used in either as a client device, application server, and/or database server, according to one embodiment.

The application server 130 is a computer or network of computers. Although a simplified example is illustrated in FIG. 2, typically the application server will be a server class system that uses powerful processors, large memory, and faster network components compared to a typical computing system used, for example, as a client device 110. The server typically has large secondary storage, for example, using a RAID (redundant array of independent disks) array and/or by establishing a relationship with an independent content delivery network (CDN) contracted to store, exchange and transmit data such as the asthma notifications contemplated above. Additionally, the computing system includes an operating system, for example, a UNIX operating system, LINUX operating system, or a WINDOWS operating system. The operating system manages the hardware and software resources of the application server 130 and also provides various services, for example, process management, input/output of data, management of peripheral devices, and so on. The operating system provides various functions for managing files stored on a device, for example, creating a new file, moving or copying files, transferring files to a remote system, and so on.

The application server 130 includes a software architecture for supporting access and use asthma analytics system 100 by many different client devices 110 through network 150, and thus at a high level can be generally characterized as a cloud-based system. The application server 130 generally provides a platform for patients 111 and healthcare providers 112 to report data recorded by the sensors associated with their medicament devices 160 including both rescue medication and controller medication events, collaborate on asthma treatment plans, browse and obtain information relating to their condition and geographic location, and make use of a variety of other functions.

Generally, the application server 130 is designed to handle a wide variety of data. The application server 130 includes logical routines that perform a variety of functions including checking the validity of the incoming data, parsing and formatting the data if necessary, passing the processed data to a database server 140 for storage, and confirming that the database server 140 has been updated.

The application server 130 stores and manages data at least in part on a patient by patient basis. Towards this end, the application server 130 creates a patient profile for each user. The patient profile is a set of data that characterizes a patient 111 of the asthma analytics system 100. The patient profile may include identify information about the patient such as age, gender, current rescue medication, current controller medication, notification preferences, a controller medication adherence plan, a patients relevant medical history, and a list of non-patient users authorized to access to the patient profile. The profile may further specify a device identifier, such as a unique media access control (MAC) address identifying the one or more client devices 110 or sensors 120 authorized to submit data (such as controller and rescue medication events) for the patient.

The profile may specify which different types of notifications are provided to patients 111 and their personal healthcare providers 112, as well as the frequency with which notifications are provided. For example, a patient 111 may authorize a healthcare provider 112 to receive notifications indicating a rescue event. The patient 111 may also authorize their healthcare provider 112 be given access to their patient profile and rescue event history. If the healthcare provider 112 is provided access to the patient profile of the patient 111, the healthcare provider may specify controller adherence or rescue medication plans. Medication plans may include a prescribed number of doses per day for controller medications.

The application server 130 also creates profiles for health care providers 112. A health care provider profile may include identifying information about the health care provider 112, such as the office location, qualifications and certifications, and so on. The health care provider profile also includes information about their patient population. The provider profile may include access to all of the profiles of that provider's patients, as well as derived data from those profiles such as aggregate demographic information, rescue and controller medication event patterns, and so on. This data may be further subdivided according to any type of data stored in the patient profiles, such as by geographic area (e.g., neighborhood, city) over by time period (e.g., weekly, monthly, yearly).

The application server 130 receives rescue medication event information from the client device 110 or the sensor 120, triggering a variety of routines on the application server 130. In the example implementations described below, the data analysis module 131 executes routines to access asthma event data as well as other data including a patient's profile, analyze the data, and output the results of its analysis to both patients 111 and providers 112. This process is generally referred to as an asthma risk analysis. The asthma risk analysis may be performed at any point in time, in response to a rescue event, due to a relevant change in the patient's environment, and in response to any one of a number of triggering conditions discussed further below.

Other analyses are also possible. For example, a risk analysis may be performed on rescue and controller medication use for multiple patients to identify based on spatial/temporal clusters (or outbreaks) of medication use based on historically significant permutations from individual, geographic, clinical, epidemiologic, demographic, or spatial or temporal baselines or predicted or expected values. Other types of analyses may include daily/weekly adherence trends, adherence changes over time, adherence comparisons to other relevant populations (e.g., all patients, patients on a particular rescue medication or controller medication or combination thereof, identification of triggers (spatial, temporal, environmental), rescue use trends over time, and rescue use comparisons to other relevant populations.

Responsive to any analyses performed, the application server 130 prepares and delivers push notifications to send to patients 111, authorized healthcare providers 112, and/or other users provided access to the patient's profile. Notifications can provide details about the timing, location, and affected patient(s) 111 involved in a medication rescue event. Notifications may additionally comprise a distress or emergency signal that requests emergency assistance that are distributed to emergency assistance providers 112. Notifications may also include the results of the asthma risk analysis performed by the data analysis module 131. More information regarding the types of notifications that may be sent and the content they may contain is further described below.

In addition to providing push notifications in response to an asthma risk analysis, notifications may also be provided as pull notifications, at particular time intervals. Additionally, some notifications (whether push or pull) may be triggered not in response to an asthma risk analysis performed in response to a rescue medication event, but instead in response to a risk analysis performed in response to one of the underlying factors in the asthma risk analysis changing, such that an updated notification is warranted. For example, if weather conditions indicate that an increase in air pollution is occurring or is imminent, this may trigger the carrying out of asthma risk analyses for all patients located in the particular geographic area where the pollution is occurring.

Notifications are provided through the network 150 to client applications 115 in a data format specifically designed for use with the client applications, and additionally or alternatively may be provided as short message service (SMS) messages, emails, phone calls, or in other data formats communicated using other communication mediums.

I.D. Database Server

The database server 140 stores patient and provider data related data such as profiles, medication events, patient medical history (e.g., electronic medical records). Patient and provider data is encrypted for security and is at least password protected and otherwise secured to meet all Health Insurance Portability and Accountability Act (HIPAA) requirements. Any analyses (e.g., asthma risk analyses) that incorporate data from multiple patients (e.g., aggregate rescue medication event data) and are provided to users is de-identified so that personally identifying information is removed to protect patient privacy.

The database server 140 also stores non-patient data used in asthma risk analyses. This data includes regional data about a number of geographic regions such as public spaces in residential or commercial zones where patients are physically located and may be exposed to pollutants. This data may specifically include or be processed to obtain a patient's proximity to green space (areas including concentrated numbers of trees and plants). One example of regional data includes georeferenced weather data, such as temperature, wind patterns, humidity, the air quality index, and so on. Another example is georeferenced pollution data, including particulate counts for various pollutants at an instance of time or measured empirically. The regional data includes information about the current weather conditions for the time and place of the rescue event such as temperature, humidity, air quality index. All of the items of data above may vary over time, and as such the data itself may be indexed by time, for example separate data points may be available by time of day (including by minute or hour), or over longer periods such as by day, week, month, or season. Although the database server 140 is illustrated in FIG. 1 as being an entity separate from the application server 130 the database server 140 may alternatively be a hardware component that is part of another server such as server 130, such that the database server 140 is implemented as one or more persistent storage devices, with the software application layer for interfacing with the stored data in the database is a part of that other server 130.

The database server 140 stores data according to defined database schemas. Typically, data storage schemas across different data sources vary significantly even when storing the same type of data including cloud application event logs and log metrics, due to implementation differences in the underlying database structure. The database server 140 may also store different types of data such as structured data, unstructured data, or semi-structured data. Data in the database server 140 may be associated with users, groups of users, and/or entities. The database server 140 provides support for database queries in a query language (e.g., SQL for relational databases, JSON NoSQL databases, etc.) for specifying instructions to manage database objects represented by the database server 140, read information from the database server 140, or write to the database server 140.

With respect to the description of FIGS. 6A-6D below, the contents of the databases described with respect to those figures may be stored in databases physically proximate to the application server 130 and separate from database server 140 as illustrated. Alternatively, those databases may be a part of database server 140, in contrast to the description of FIGS. 6A-6D illustrating them as being within data analysis module 131. This and other variations thereupon are within the scope of this description.

I.E. Network

The network 150 represents the various wired and wireless communication pathways between the client 110 devices, the sensor 120, the application server 130, and the database server 140. Network 150 uses standard Internet communications technologies and/or protocols. Thus, the network 150 can include links using technologies such as Ethernet, IEEE 802.11, integrated services digital network (ISDN), asynchronous transfer mode (ATM), etc. Similarly, the networking protocols used on the network 150 can include the transmission control protocol/Internet protocol (TCP/IP), the hypertext transport protocol (HTTP), the simple mail transfer protocol (SMTP), the file transfer protocol (FTP), etc. The data exchanged over the network 150 can be represented using technologies and/or formats including the hypertext markup language (HTML), the extensible markup language (XML), etc. In addition, all or some links can be encrypted using conventional encryption technologies such as the secure sockets layer (SSL), Secure HTTP (HTTPS) and/or virtual private networks (VPNs). In another embodiment, the entities can use custom and/or dedicated data communications technologies instead of, or in addition to, the ones described above.

II. Example Computing Devices

FIG. 2 is a high-level block diagram illustrating physical components of an example computer 200 that may be used as part of a client device 110, application server 130, and/or database server 140 from FIG. 1, according to one embodiment. Illustrated is a chipset 210 coupled to at least one processor 205. Coupled to the chipset 210 is volatile memory 215, a network adapter 220, an input/output (I/O) device(s) 225, a storage device 230 representing a non-volatile memory, and a display 235. In one embodiment, the functionality of the chipset 210 is provided by a memory controller 211 and an I/O controller 212. In another embodiment, the memory 215 is coupled directly to the processor 205 instead of the chipset 210. In some embodiments, memory 215 includes high-speed random access memory (RAM), such as DRAM, SRAM, DDR RAM or other random access solid state memory devices.

The storage device 230 is any non-transitory computer-readable storage medium, such as a hard drive, compact disk read-only memory (CD-ROM), DVD, or a solid-state memory device. The memory 215 holds instructions and data used by the processor 205. The I/O device 225 may be a touch input surface (capacitive or otherwise), a mouse, track ball, or other type of pointing device, a keyboard, or another form of input device. The display 235 displays images and other information from for the computer 200. The network adapter 220 couples the computer 200 to the network 150.

As is known in the art, a computer 200 can have different and/or other components than those shown in FIG. 2. In addition, the computer 200 can lack certain illustrated components. In one embodiment, a computer 200 acting as server 140 may lack a dedicated I/O device 225, and/or display 218. Moreover, the storage device 230 can be local and/or remote from the computer 200 (such as embodied within a storage area network (SAN)), and, in one embodiment, the storage device 230 is not a CD-ROM device or a DVD device.

Generally, the exact physical components used in a client device 110 will vary in size, power requirements, and performance from those used in the application server 130 and the database server 140. For example, client devices 110, which will often be home computers, tablet computers, laptop computers, or smart phones, will include relatively small storage capacities and processing power, but will include input devices and displays. These components are suitable for user input of data and receipt, display, and interaction with notifications provided by the application server 130. In contrast, the application server 130 may include many physically separate, locally networked computers each having a significant amount of processing power for carrying out the asthma risk analyses introduced above. In one embodiment, the processing power of the application server 130 provided by a service such as Amazon Web Services™. Also in contrast, the database server 140 may include many, physically separate computers each having a significant amount of persistent storage capacity for storing the data associated with the application server.

As is known in the art, the computer 200 is adapted to execute computer program modules for providing functionality described herein. A module can be implemented in hardware, firmware, and/or software. In one embodiment, program modules are stored on the storage device 230, loaded into the memory 215, and executed by the processor 205.

III. Dashboard

Figure 3A:
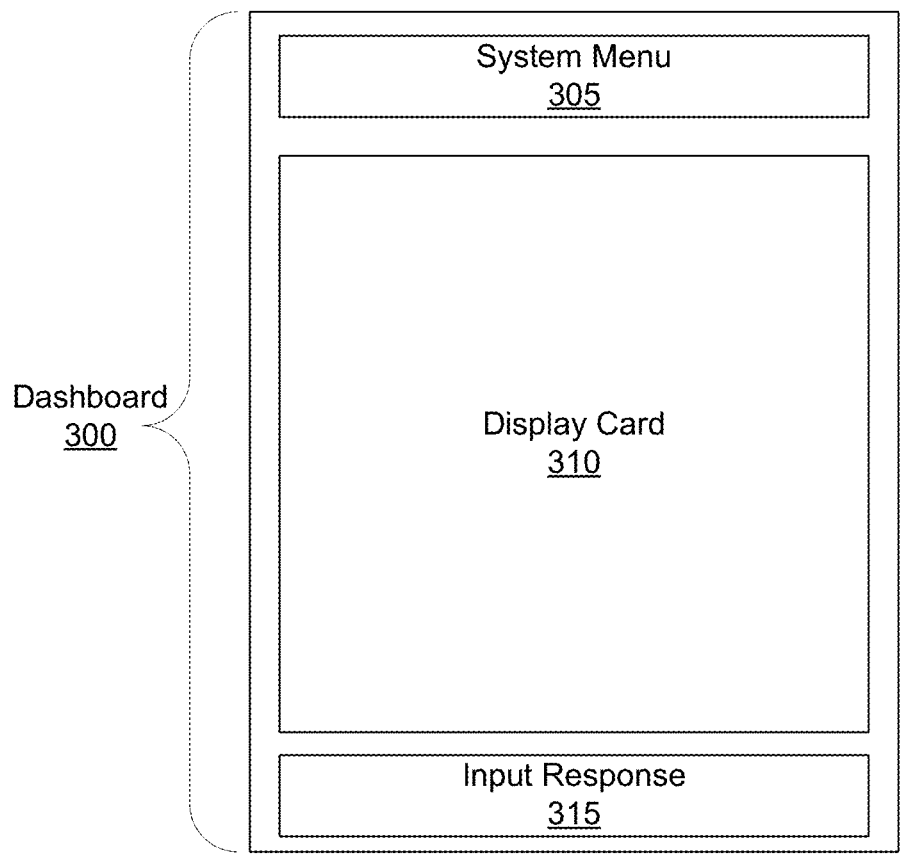
FIG. 3A shows a dashboard of a client application that allows a user to interact with an asthma analytics system, according to one embodiment.

The dashboard, for example dashboard 300 illustrated in FIG. 3A, allows users to interact with the asthma analytics system 100. The dashboard 300 provides a means to transfer information on a user-to-user (e.g., patient 111 to provider 112) or user-to-system/system-to-user basis. Dashboards 300 are accessed through the client application 115 on the client device 110 and provide a mechanism for both patients and healthcare providers to monitor medication rescue events, exchange personalized patient healthcare information, and receive notifications such as asthma rescue event risk notifications. Patients may communicate with other health care providers and other patients through the dashboard 300, for example, to discuss and share information about asthma, medication usage, or asthma management. The ability to share asthma healthcare information may give patients or healthcare care providers experiencing a similar issue a way to share individual perspectives.

The dashboard 300 also allows authorized health care providers 112 to access a list of patients to view, annotate, update, interact with, and export information about asthma patient and community data and statistics in various demographics or geographic segments. Using the dashboard 300, healthcare providers are able to monitor patients individually or in aggregate, to receive and provide feedback on how their associated patient populations are responding to asthma management guidance. A healthcare provider who has access to individual or multiple patients has the ability to establish notification thresholds, set parameters for the notifications, and receive notifications when patients' event history matches certain conditions (e.g. rescue event). Additionally, the dashboard 300 can receive and display regular reports of event patterns for specific demographic generated by the asthma analytics system 100.

The dashboard 300 presents a variety of information including tabular data, graphical visualizations, and analyses to users through display "cards" 310. Display cards 310 are conformably suited to smaller displays typical of portable client devices 110, for example mobile phones or tablets, and include "bite size" pieces of information that mimic the simplistic organizational style found in baseball cards. The dashboard 300 may also include a system menu 305 that allows users to navigate through different categories of healthcare information.

Notifications provided by the application server 130 are related to the display cards 310. Generally, notifications include not only information to be presented to the user through the application 115, but also parameters for specifying which display card 310 is to be used to display the contents of the notification. Any information pushed/pulled from the application server 130 may be associated with one or more cards. For example, a notification can be pushed to the patient based on the outcome of an asthma risk analysis. The dashboard 300 will process the notification and determine which card/s to use to present the information in the notification. Continuing the example, the recipient of the notification may make a request to pull data from the application server 130. The application server 130 provides the requested data in another notification, and the dashboard 300 then determines which display card 310 to display the requested information.

To interact with information presented, some display cards 310a include a input response 315 area. For example, in the display card 310b illustrated in FIG. 3B, a patient may scroll up or down in the input response 315 area to select a controller medication used to manage asthma or select the "next" to move to an additional display card 310.

The dashboard 300 may provide a variety of different display cards 310, which may be organized into categories. An information card type includes cards that display data. Information cards may, for example, display medication rescue events, statistics, and maps including both patient data and community data. Information cards are further sub-categorized into event, trend, education, and alert display cards.

Figure 3B:
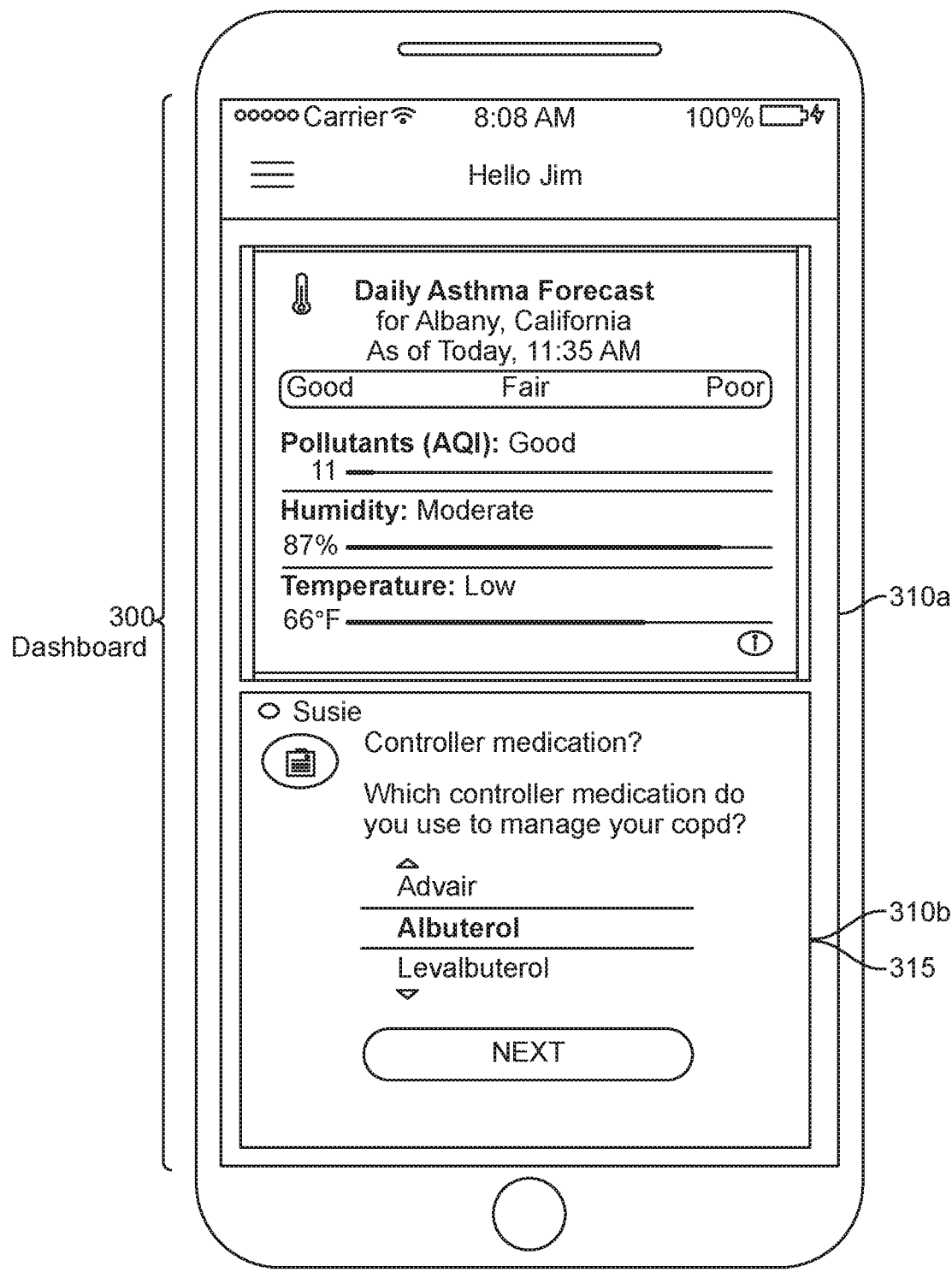
FIG. 3B shows an example card displayed within the dashboard of the client application, according to one embodiment.

Event cards include data relating to rescue medication events, such as a list of historical medication rescue events for a specific patient, or patient rescue event data overlaid on a geographical map for a specific provider. For example, the display card 310a illustrated in FIG. 3B is an event card that highlights patients experiencing asthma rescue events in a particular geographic area. Another event card may display an example medication usage report including a map of the location of a rescue usage event, environmental conditions at the location, and an input response area 315 for the recipient to add triggers for the rescue usage event. Another event trend card may display rescue device usage for the previous week including a total number of uses for the time period and a number of uses for each day.

A trend card includes statistical information presented using a graph or a chart designed for clear comprehension by the recipient. Examples of trend cards include plots of asthma rescue events over various time periods, time of day trends, days of week trends, and trigger trends.

An education card includes information meant to educate the recipient. Education cards provide general disease information and tips for patients to reduce their risk of rescue events. Some education cards may require an input response 315 to allow recipients to specify whether the information provided is relevant or interesting for use in serving future cards.

Alert cards notify users of important information including informing a recipient that they are at risk for an event and/or that data has not been received from a device over a recent time period. Other alerts may include an alert that a setting on the client device is preventing data syncing (e.g. Blue tooth is turned off) or that a patient's asthma risk score has changed.

A survey card type solicits a user response by presenting yes/no, multiple choice, or open-ended questions for the user to respond to. For example, a healthcare provider or the asthma analytics system 100 may send a survey card with an asthma-related questionnaire to a patient 111 to determine a level of disease control for a specific patient. Additionally, a survey card may request the type of controller medication that the patient 111 uses to treat asthma symptoms. Generally, survey cards provide the application server 130 with data that may be missing from a patient's medical history or patient profile (as introduced above), and/or provide an update to potentially outdated information. One or more survey cards may be used to complete the patient enrollment process and create a patient profile for storage in database server 140. For example, when a patient 111 initially enrolls in the asthma analytics system 100, a push notification will be triggered by the application server 130 prompting the patient 111 to create a patient profile.

Example of survey cards may include a survey question asking whether a patient has made any emergency room visits as a result of asthma rescue events, information about the patient's controller medication, how many times the patient used their rescue medication to control an event, and what their controller medication daily schedule is. Survey cards may also ask about a patients asthma triggers, such as whether pollen is a trigger. Some survey cards may ask a patient to rate their general quality of life on 5-point Likert scale, to rate their quality of sleep, to rate their ability to be active over last 7 days, and so on. Other survey cards ask whether the patient feels better or worse than yesterday, whether the patient has had to go to emergency room or hospital in last 12 months for a rescue event and so on.

In some instances, patient behavior or sensor-reported event information that is inconsistent with existing patient information may trigger the sending of a survey card in order to resolve ambiguity as to the patient's circumstances. For example, if the patient is experiencing a greater-than-expected count of asthma events, the survey card may request information about the type of medication the patient has currently listed on their medicament device 160, in order to verify that the correct medication is being used. Another example includes if the reported information about controller medication use indicates that the patient is only using the controller medication one time per day but their adherence plan indicates they are supposed to be taking their controller medication twice per day, system 100 could send a notification asking if the patient needs to change their adherence plan.

In some instances, patient behavior or sensor-reported event information that is inconsistent with existing patient information may trigger the sending of a survey card in order to resolve ambiguity as to the patient's circumstances. For example, if the patient is experiencing a greater-than-expected count of asthma events, the survey card may request information about the type of medication the patient has currently listed on their medicament device 160, in order to verify that the correct medication is being used. As another example, if the reported information about controller medication use indicates that the patient is only using the controller medication one time per day but their adherence plan indicates they are supposed to be taking their controller medication twice per day, system 100 could send a notification asking if the patient needs to change their adherence plan.

Navigation cards represent actionable data or messages that, upon user interaction, may redirect the user to another screen or card that is part of the dashboard 300. For example, if a patient wants to share information or request specific medication plans for controller medications with a physician, a navigation card would be used to facilitate the sharing of information or enrollment in controller adherence plan. Additionally, navigation cards allow users to update information surrounding medication rescue events.

Adherence cards are designed to encourage a patient to continually use their controller medication on schedule over different periods of time. Adherence cards may indicate a "streak" or continuous run of on-time controller medication events, a better performance in aggregate even if not streak has been Additionally, a survey card may inquire as to the patient physical state in response to recording a significant number of rescue events within a threshold period of time of each other. Controller medication events may be represented as graphs to illustrate when the patient 111 did and did not take their controller medication on time during various periods during the day, as prescribed by their health care provider 112. Cards may also detail a daily schedule for controller medication and an indicator for displaying whether the scheduled dose has been taken. For example, a red "X" may indicate the scheduled dose has not been taken, but a green check mark or a different symbol may indicate that the scheduled dose has been taken.

Setup cards guide recipients in associating sensors with client devices 110. Setup cards may guide pairing a sensor to a client device 110 using Bluetooth, prompt the recipient to initiate the pairing process or prompt the user to select a sensor device for pairing, or notify the user that the sensor is paired.

In some embodiments, the dashboard may present a user interface. The user interface may illustrate a list of rescue events, responsive to the user's selection of the "View Timeline" input response area 315c. The list displays rescue usage events over a time period and includes details such as date, time, number of puffs, and location. Recipients may edit rescue usage events and/or add additional details by selecting the edit interaction response areas. Some interfaces may present an event summary for a rescue usage event to the user. The event summary may be presented to the user in response to the user selecting the edit interaction response area of the user interface. From the dashboard, the user may also view and edit a medication list, detailing information such as medication type (rescue, controller, etc.), dosage schedule, and sensors.

IV. Event-Driven Asthma Risk Notifications

To receive asthma risk notifications, a patient interfaces with the dashboard 300 to initialize a patient profile. Once the patient completes their patient profile, the client device 110 transmits the patient profile for use b the application server 130 and storage by the database server 140. Once a patient's patient profile is initialized, the application server 130 may begin to receive rescue medication events detected by the sensor 120 associated with the patient's medicament device 160. This initialization process for the patient profile is only performed once during the patient's first use of the medicament device.

Upon the sensor detecting a rescue usage event, the patient device 111 collects and sends the rescue event data to the application server 130, where the event information is stored 415. In some embodiments, this detection and storage process is performed repeatedly at any detection of a rescue usage event. However, this frequency may differ from the frequency with which a risk analysis is performed.

Figure 4:
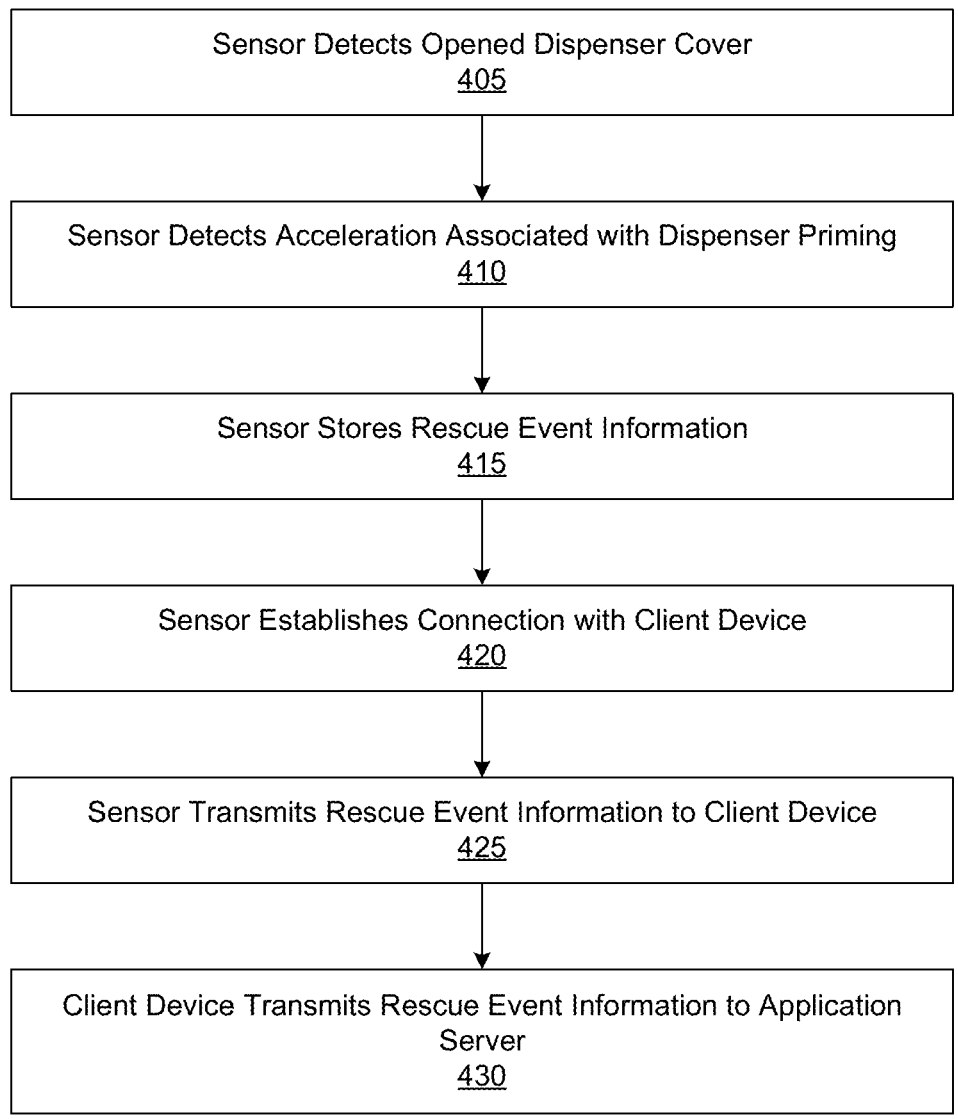
FIG. 4 is a flowchart for detecting a rescue medication event by an asthma analytics system, according to one embodiment.

Referring now to FIG. 4, the application server 130 generally receives a rescue event anytime the patient uses their rescue medicament dispenser 160 to relieve asthma-related event symptoms. As an example of the process for capturing such an event for a particular device 160/sensor 120 combination, at the start of symptoms, the sensor 120 may detect 405 whether a medication dispenser 160 cover is opened. When the medication dispenser cover is opened, the sensor 120 may detect 410 an acceleration associated with a priming of the dispenser 160. For some types of medicament dispensers, the "priming" includes activating a mechanism to release a dose of a medication from a packaging. In other types of medicament dispensers, the "priming" includes a rapid shaking of a medication canister.

After the priming action is detected, the sensor 120 is configured to store 415 data associated with the rescue event in active memory of the sensor 120. The rescue event data may include information that describes the time and date of associated with the rescue event, the status or condition of the medicament device 160 (e.g. battery level), the number of doses of medication remaining (before or after the event), self-test results, and physiological data of a patient being treated with the medicament device 160 as measured by the sensor 120. As soon as the sensor establishes 420 a network connection with either the client device 110 or network 150, the sensor transmits 425 any locally stored rescue event data to the client device 110 or the application server 130. If the event data was transmitted to the client device 110 first, the client device 110 then transmits 430 the rescue event data to the application server 130 as soon as the client device 110 establishes a network connection with the network 150. Depending upon the implementation, either the client device 110 or sensor 120 will add the geographic location where the event took place to the event data transmitted to the application server 130.

Upon receiving and storing the rescue usage event data, the application server 130 may request further information from the patient describing the rescue usage event. To obtain the information, the application server 130 generates a push notification, including the questions to be asked, to be sent to the patient's client device 110. The client device 110 may present the push notification as a survey type card 310. The patient may respond to the request by providing inputs 315 in response to the survey card 310. Alternatively, the patient 111 may elect not to respond to the request. This is permissible, any gaps in information may be obtained through later push notifications, or upon entry by provider 112 after a meeting with the patient 111. In one implementation, the failure to receive the additionally requested data in response to request does not hold up the remainder of the analysis described in steps 425-445.

The information collected as part of the event or otherwise may identify 420, information pertaining to parameters that may have played a role in triggering the event, a location of the rescue event, a label (e.g., work, home, or school) for the location, a rating to signify the personal importance of the location to the patient, and whether the use was pre-emptive (e.g., medication taken prior to exercising) in addition to any other relevant information.

In addition to requesting additional event data, the application server 130 accesses 425 stored contextual data from the database server 140. Generally, contextual data refers data other than event data, which includes but is not limited to: to atmospheric conditions, weather conditions, air quality conditions, pollen data, patient data recorded from past rescue usage events, and any other considerations that are not directly detected by the medicament device at the time of the rescue usage event. By contrast, event data refers to any parameters related to the rescue event and reported by the medicament device, such as medication dosage, the time of the event, the location of the event, and relevant adherence data. Both forms of data may include temporally-current information as well as stored historical data. Accordingly, as part of obtaining the contextual data, the application server 130 also accesses historical rescue usage event data for the patient 111. This historical data can include all of the data from any past controller or rescue medication event data from the patient's history over a variety of windows of time in the past, and each historical event may include all of the same items of information as was reported 410 for this event along with any data collected upon follow up thereafter.

However, note that in the following description, such as in FIGS. 6 and 7, in some instances contextual data and historical data are represented separately. Contextual data may be used to refer to geographic and regional information relevant to the current event or current location of the patient's client device 110, whereas historical data may be used to refer to geographic, regional, and event information from previous rescue usage events from the same or different patients.

IV.A Asthma Trigger Identification Overview

When considered individually, asthma rescue inhaler usage events provide little insight in to the specific causes of the rescue event, however these events include data that is useful in identifying correlations between rescue events. For example, if only a single rescue event is analyzed, the asthma event contextual environmental data may not conclusively indicate what specific conditions caused the rescue event. However, that single event does at least indicate that certain conditions were present during the event. When the contextual data for an individual event is considered in addition to the contextual data from several other related or similar events, the data analysis module 131 may identify, with a high level of confidence, which triggers a patient is and is not sensitive to.

Figure 5:
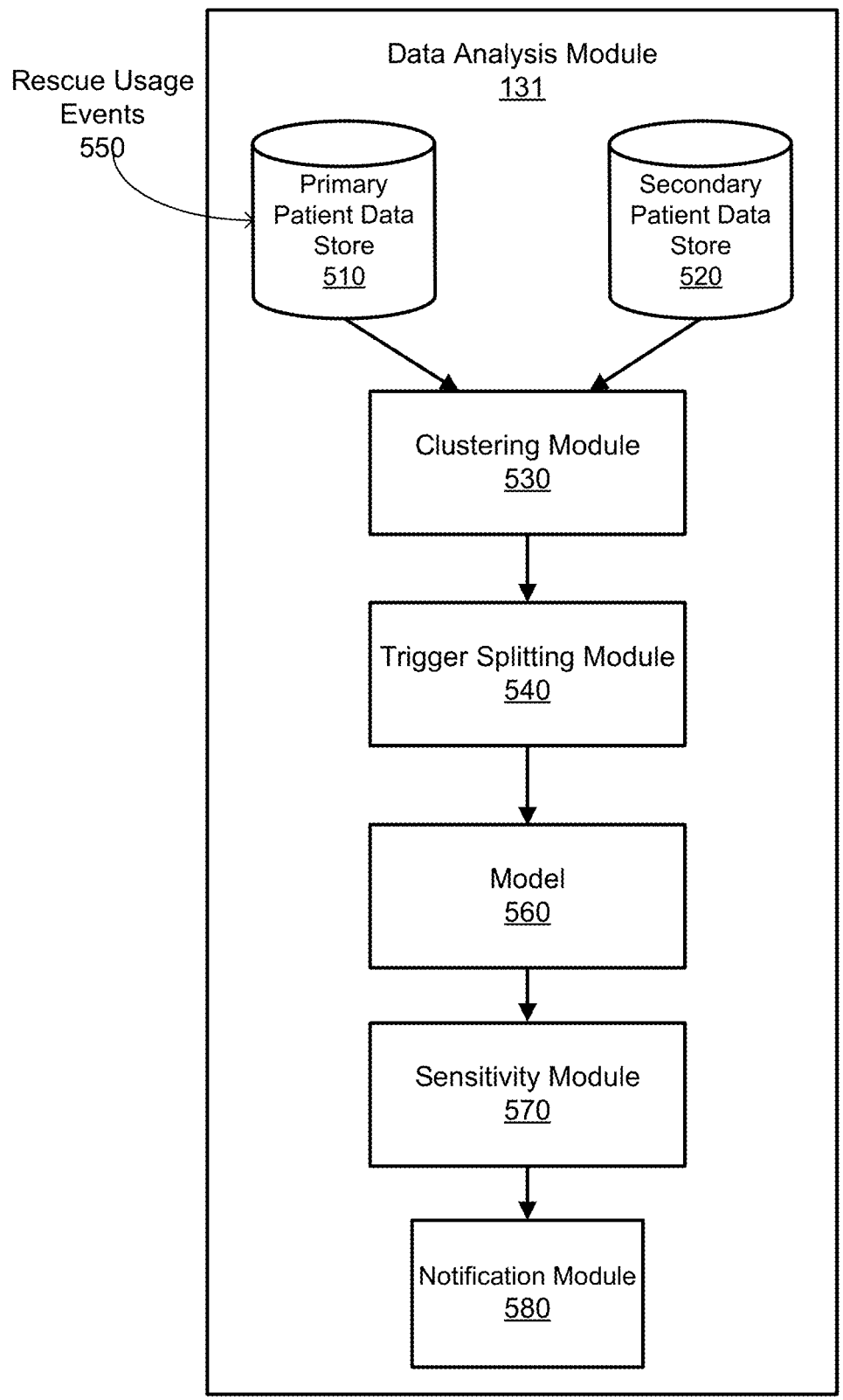
FIG. 5 is a block diagram illustrating the modules within the data analysis module, according to one embodiment.

In one embodiment, the process for determining triggers for a patient are carried out by the data analysis module 131 of the analytic system 100 introduced above. FIG. 5 is a block diagram illustrating the logical components that carry out the functions of the data analysis module 131, according to one embodiment. The analytics system 100 includes, on the application server 130, a data analysis module 131 that analyses the variety of data collected by the system, introduced above and discussed further below, to identify triggers for patients at risk of experiencing rescue inhaler usage events. These trigger analyses are used to generate notifications that are specifically configured to be sent to a patient in a sufficiently timely manner to hopefully avoid or anticipate the occurrence of a respiratory event, such as an asthma or COPD event, which would necessitate usage of their rescue inhaler.

The logical architecture of the data analysis module 131 comprises a primary patient data store 510, a secondary patient data store 520, a clustering module 530, a trigger splitting module 540, a model 560, a sensitivity module 570 and a notification module 580. Functionality indicated as being performed by a particular module (or store) may be performed by other modules (or stores) instead.

The analysis of patient-specific triggers for rescue inhaler usage events by module 131 is based on patient data for a population of patients, for example contextual data, demographic data, and clinical data. As described herein, the patient in question for whom the module 131 is determining triggers is referred to as the "primary patient" and each other patient of a set of similar patients is referred to as a "secondary patient." The primary patient data store 510 includes contextual information describing every day that the patient has been associated with the rescue inhaler. The primary patient data also includes demographic and clinical data describing the medical condition of the primary patient and their medication regimen. Similarly, the secondary patient data store 520 stores demographic, clinical data, and contextual data for the other patients of the set. The set of similar patients may be determined according to a number of methods. As one example, using the set of other patients may be determined by those patients who use a rescue inhaler connected over a same network 150 (e.g., 3G cell phone tower router, local internet service provider, etc., thus grouping patients geographically. For example, if one hundred patients use rescue inhalers communicating with the network 150, the primary patient store 510 stores data associated with one user (for whom triggers are being determined at that instant) and the secondary patient data store 520 stores data associated with the remaining ninety-nine. Other methods may use other criteria, such as based on contextual data, demographic data, or clinical data, specific examples of which are provided below.

Primary patient data and secondary patient data generally include the same information, including contextual data, demographic data, and patient data.

Contextual data describes days during which one or more rescue events did occur and days during which no rescue usage events occurred. The primary patient data store 510 may also include a record of the user's behavior over the first one month in which they are using the sensor 120 with the medicament device 160. Contextual data includes, but is not limited to, air pollutant conditions (e.g., ozone molecules (o3), nitrogen dioxide molecules (no2), sulfur dioxide molecules (so2), particulate matter, 2.5 micrometers or less ($PM_{2.5}$), particulate matter, 10 micrometer or less ($PM_{10}$), air quality index) and weather condition (e.g., temperature, humidity, wind speed, wind direction, station pressure, and visibility). Each contextual condition also represents a potential trigger or a condition which contributes to or stimulates a rescue inhaler usage event. Generally, the contextual data may be gathered automatically based on device or other third party data reporting, manually provided by a patient and/or provider, or otherwise obtained. Rescue inhaler usage events and other contextual data may also be identified based on where the event temporally occurred while the sensor 120, client device 110, and/or medicament device 160 were physically located within the boundary of a geographic region.

Demographic data describes each patient including, but not limited to the gender, age, and the base location of each user. The base location refers to a geographic region within which the patient spends a majority of their time, for example a home address or an office address. The size of the geographic region may range depending on the frequency of a patient's rescue inhaler usage and their level of risk, for example 500 feet areas, latitude/longitude coordinates, zip codes, city boundaries, etc. Demographic data may be entered manually by the patient through the GUI 300 when setting up use of the sensor 120 or provided to a healthcare provider for association with their system.

Patient data may also include clinical information, for example, the medication type, the prescription amount, the prescription data, the dosage of medication taken, and the adherence regimen comparing the frequency per day with which the patient takes the rescue medication to the frequency with which the prescription is instructed to take the rescue medication. Patient data is generally entered by the healthcare provider, but may also be entered by the patient manually.

Individual primary patients may be more susceptible to specific trigger conditions than other patients. As described herein, a trigger refers to a measurable quantity, for example an environmental condition, which independently or in combination with one or other triggers exacerbates a patient's condition thereby causing a rescue inhaler usage event. For example, under conditions with higher levels of humidity, one patient may be more at risk of an asthma rescue usage event than another patient. Accordingly, the model 560 determines which, if any, triggers are relevant to each patient, as well as a relative risk of to the patient for each trigger.

During normal course, the data stores 510/520 receive data regarding rescue usage events 550 as they occur and updates the data stores to reflect the contextual data associated with the recent current rescue usage events. The frequency with which a data store is updated with new rescue usage events 550 may vary depending on a number of factors not limited to the patient's circumstances, their adherence regimen to a controller medication, environmental conditions, and so on. A patient's adherence to a prescribed controller medication regimen is a comparison between the frequency per day that the patient uses the controller inhaler unit and the frequency per day that the patient was instructed to use the controller inhaler unit and may be measured based on the usage of a controller inhaler unit.

For a given patient, the clustering module 530 receives input from the primary patient data store 510 (regarding that patient) and the secondary patient data store 520 (regarding the other patients, as distinguished above) to generate an aggregate dataset to be inputted to the model 560. An aggregate dataset includes an aggregation of contextual data from each day that the user has been in possession of the rescue usage inhaler (e.g., the sensor 120 and medicament device 160 combination). For each of those days, the aggregate dataset includes a separate feature vector (together forming an array of feature vectors) describing the conditions for a set of trigger conditions and a label indicating whether or not at least one rescue event occurred. In one implementation, the feature vector has a fixed number of dimensions (or elements). In one embodiment, the number of elements is the number of the possible triggers considered by the data analysis module 131). Each element stores a feature value (also referred to as a trigger value) for each trigger including measured value corresponding to that trigger during that day or based on the received rescue inhaler usage event. Often, these trigger values are numerical values such as integers, for example a temperature reading of 60° C., however in some embodiments they may also be floating point values or categorical values (e.g., is a given condition present or not present).

In implementations in which sufficient primary patient data has been collected, the clustering module generates an aggregate dataset comprised solely of primary patient data, specifically feature vectors of data from primary patients. Sufficient primary patient data allows the data analysis module 131 to identify the primary patient as sensitive or insensitive to each trigger condition with a high level of confidence based only on that patient's data. However, identifications made with a high level of confidence require large amounts of data which would require primary patients to have been using their rescue inhaler usage for an extended period of times, for example multiple months to years. Accordingly, to expedite the time required for the data analysis module 131 to confidently identify trigger conditions for relatively new patients, the clustering module 530 uses data (feature vectors) from secondary patients who are demographically, contextually, and clinically similar to the primary patient to supplement the aggregate dataset in order to make these determinations with higher confidence. Thus, in these instances aggregate datasets including data from both the primary patient and secondary patients. The aggregate dataset is further described below in reference to FIG. 9.

The trigger splitting module 540 receives the aggregate dataset and reconfigures the feature vector for each day into a converted format. In one embodiment, the trigger values are assumed to be integers. In this embodiment, for each trigger value in the aggregate dataset, the trigger splitting module 540 replaces a single trigger and corresponding integer trigger values with a set of similar triggers each corresponding to a different possible integer values for the trigger, each of these similar triggers having a binary label: a first label (e.g., 1) indicating whether the trigger was present in that feature vector (e.g., for that day) and a second label (e.g., 0) indicating the trigger was not present in that feature vector.

Thus, whereas previously the feature vector had only a single entry for a trigger with a corresponding integer value (e.g., temperature, with the value being the temperature in Celsius), the converted format of the aggregate dataset has a number of triggers, one for each possible value of the unconverted trigger, with the value for each converted trigger indicating a binary value of whether the original value for that trigger for that day is greater or less than the integer value of that particular trigger. Continuing with the temperature example, the single temperature trigger would be replaced with a "temperature>10° C." trigger, a "temperature>11° C." trigger, a "temperature>12° C." trigger, and so on, where the binary values for these triggers indicate the temperature on that day. The trigger splitting module 540 will be further described in reference to FIG. 8.

In order to perform a trigger analysis to determine a relative risk score for each trigger, a model 560, receives the contextual data stored within the aggregate dataset as input to the model's function to determine a patient's relative risk for individual triggers of asthma, COPD, or other respiratory diseases. The model 560, for example a mathematical function or other more complex logical structure is trained using the contextual data from the primary patient and, if applicable, any secondary patients.

In one implementation, the model 560 determines a baseline threshold based on the total number of usage events over a specified prior time period preceding either the current day during which the risk is being calculate (for either labeling during training or during model use), or more generally during a time period preceding the time of a current/most recent rescue usage event. The baseline (also referred to as the baseline threshold) describes a maximum number of rescue usage events that may be recorded in a single day for that day to still be labeled as a low risk day by the data analysis module 131. In alternate implementations, the model 560 implements different techniques to generate the baseline threshold, for example an average of the number of rescue usage events per day.

The model 560 identifies any feature vectors within the aggregate dataset, associated with either a primary or secondary patient, describing a day during which the number of recorded rescue usage events exceeded the baseline threshold. The identified days exceeding the baseline threshold may collectively be referred to as exacerbation days.

For each trigger, the model 560 separates the exacerbation days into two groups based on the label assigned to the trigger value for that day (i.e., days during which the trigger was present and days during which the trigger was not present). For example, when evaluating the "temperature>15° C." trigger, the model 560 separates exacerbation days into days during which the temperature exceeded 15° C. and days during which the temperature was below 15° C. For each group of exacerbation days, the model 560 determines a relative exacerbation by calculating the ratio of exacerbation days in the group to the total number of days included in the aggregate dataset. Thus, there are two relative exacerbations for each trigger, one when the trigger is present, and one when the trigger is not. In other embodiments, other calculations other than or in addition to a ratio calculation may be used to determine the relative exacerbation.

Using the relative exacerbations for the triggers, the model 560 determines a relative risk score by determining the difference between the relative exacerbations for each of the two groups for that trigger. For example, if the relative exacerbation when a trigger is present is 10% and the relative exacerbation when the same trigger is not present is 10%, the model 450 may determine a relative risk score of 0 indicating that the trigger does not pose a serious risk of rescue usage event to the primary patient. Alternatively, if the relative exacerbation when a trigger is present is 90%, and the relative exacerbation when the same trigger is not present is 10%, the model may determine a relative risk score of 1 or some other non-zero numerical value corresponding to the magnitude of the difference between the trigger-present and trigger-not-present group. The model 560 and relative risk score calculation are further described in Section IV.C.

The exact manner in which the relative risk score for a trigger is determined may vary by implementation. In one embodiment, the relative exacerbation is a function of a difference between the relative exacerbations of the two different groups/labels. In this case, the larger the difference, the more indicative the condition associated with the trigger was responsible for the increased count of exacerbation days when the trigger was present.

The sensitivity module 570 receives the relative risk score and a count of the days during which the trigger was present to perform a statistical analysis of the relative risk score. More specifically, the sensitivity module 570 may determine the significance, confidence, and magnitude of the relative risk score based on a comparison to one or more confidence intervals. If the comparison to the confidence intervals indicates that the relative risk score exceeds a threshold confidence level, the sensitivity module 570 labels the user as sensitive to the trigger. In implementations in which the relative risk score does not exceed a threshold confidence level, the sensitivity module 750 labels the user as insensitive to the trigger.

In some implementations, the threshold confidence level may be adjusted depending on data such as the count of exacerbation days, the count of days including a rescue usage event, as well as primary patient data vs. secondary patient data. This helps ensure that the confidence level accounts for varying amounts of data that may be available to make the trigger labeling determination. In one embodiment, the threshold confidence level is set higher if there is comparatively more data available (either in general or for the primary patient specifically), and set lower if comparatively little data is available. The threshold confidence level may also be adjusted based on the contents of the data available, for example the value of the relative risk score, the number of rescue usage events in the presence or absence of the a trigger, etc.

Once a patient has been determined to be sensitive to a trigger by the data analysis module 131, the notification module 580 generates a risk score notification including any one or more of the following: a list of labeled triggers, a list of triggers still being analyzed, information characterizing the trigger, the relative risk score and confidence interval of the trigger, and options that the patient may take to prevent the occurrence of another rescue usage event in the presence of the trigger. The notification may be in the form of a card delivered through the dashboard 300 as discussed above to the client device 110. The notification may also be provided to the healthcare provider's client device 110.

Figure 6:
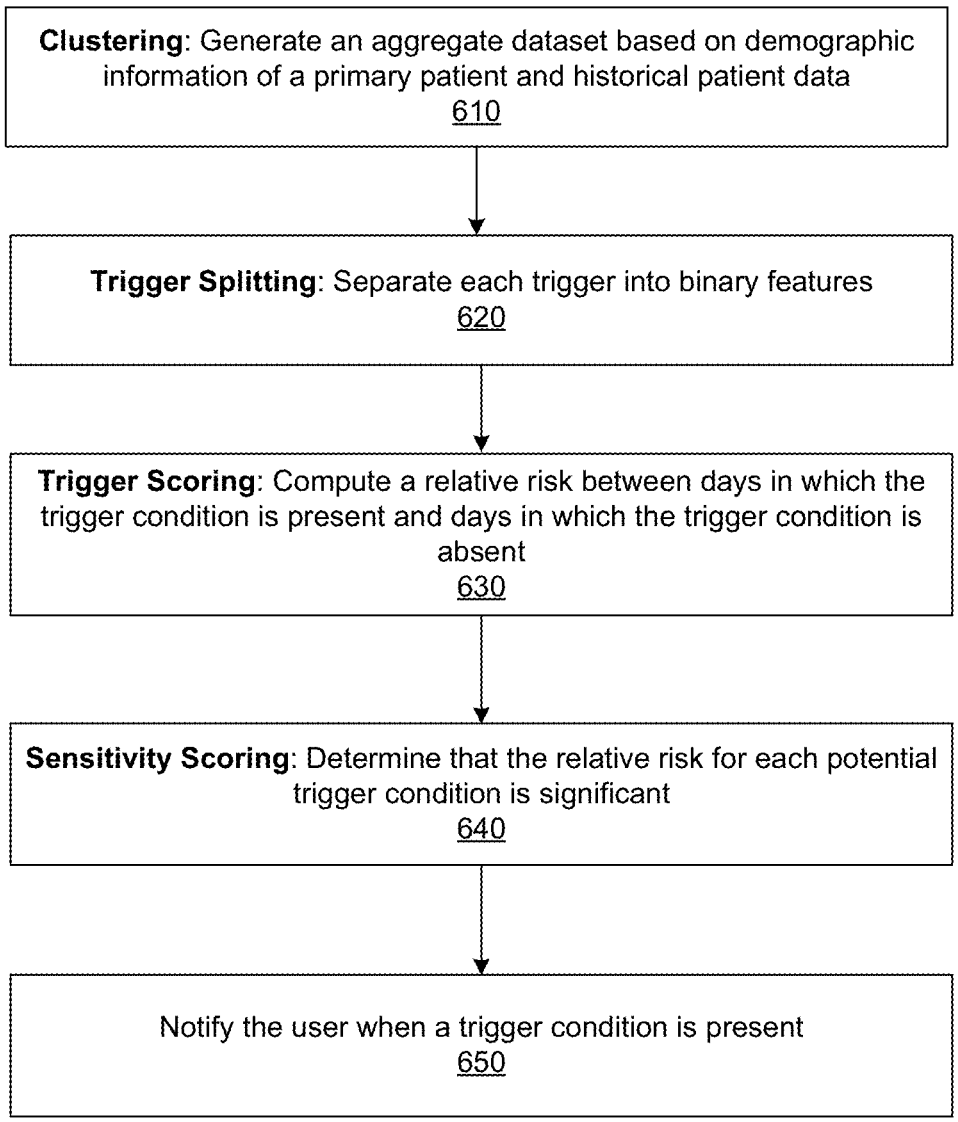
FIG. 6 is a flowchart for identifying triggers for individual patients, according to one embodiment.

FIG. 6 is a flowchart for identifying triggers for a primary patient by implementing the techniques described above, according to one embodiment. Starting with demographic and clinical information and contextual data received from the primary patient data store 510, the clustering module 530 executes a clustering protocol to generate 610 an aggregate dataset. The clustering module 530 identifies secondary patients from the secondary patient data store 520 sharing similarities with the primary patient and adds feature vectors describing their own contextual data on the same days as the feature vectors associated with the primary patient. The trigger splitting module 540 executes a trigger splitting protocol to separate 620 each trigger into a binary set of trigger conditions. The trigger splitting module 640 receives the aggregate dataset from the clustering module 530 and determines a range of all potential values for each triggers. The trigger splitting module 540 identifies a critical value and bifurcates the range of potential values into two ranges, each of which is associated with a specific label describing the presence of the trigger.

The model 560 receives the compressed aggregate dataset from the trigger splitting module and executes a trigger scoring protocol to computes 630 a relative risk score for each trigger. The relative risk score is based on the number of days during which the trigger was present and at least one rescue usage event occurred, the number of days during which the trigger was not present and at least one rescue usage event occurred, and the total number of days for which a feature vector is stored within the aggregate dataset. The sensitivity module 570 receives the relative risk score for each trigger from the model 560 and executes a sensitivity scoring procedure to determine 640 whether the relative risk score exceed a threshold confidence level. For triggers determined to exceed the threshold confidence level for the primary patient, the notification module 580 notifies 650 the user of the trigger and when the trigger is present with information or recommendations to address the trigger.

IV.B Generating an Aggregate Dataset

IV.B.1 Clustering Protocol

As described above, the clustering module 530 identifies and includes contextual data describing secondary patients who share similarities with the primary patient in the aggregate dataset when insufficient primary patient data exists for the data analysis module 131 to label a patient as sensitive to each of a set of triggers. The secondary patient data supplements the recorded primary patient data allowing the data analysis module 131 to perform trigger analyses based on larger volume of data and with a greater amount of confidence in the results.

Figure 7:
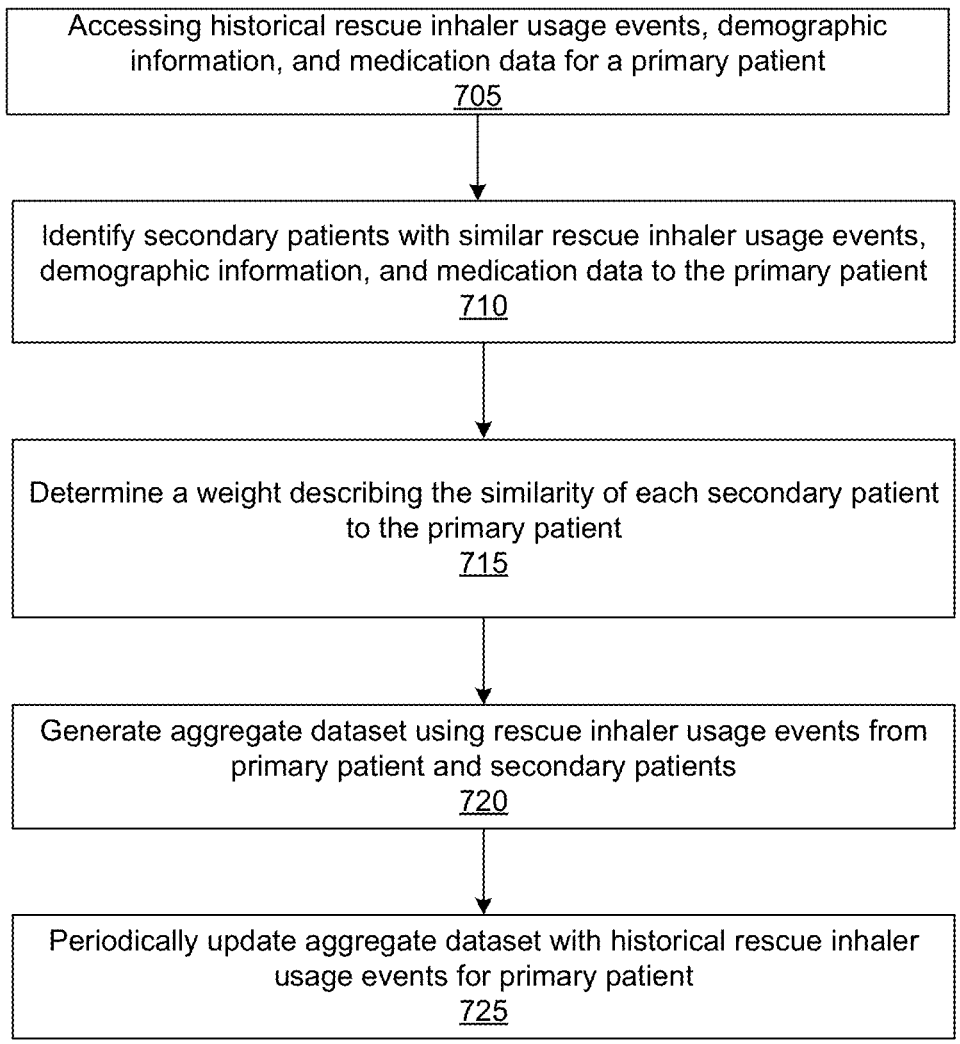
FIG. 7 is a flowchart for aggregating patient data into a dataset, according to one embodiment.

FIG. 7 is a flowchart for generating an aggregate dataset, according to one embodiment. FIG. 7 illustrates an implementation of the clustering protocol previously described in reference to FIG. 6. The clustering module accesses 705 historical rescue inhaler usage events, demographic information, and medication data for the primary patient. During the initialization of the patient profile of the primary patient, the primary patient data store 510 receives and stores demographic data, for example the age and gender of the primary patient, the medication type taken by the patient, and the dosage of the medication taken by the patient. However, in order to accurately identify secondary patients who are similar to the primary patient, the clustering module 530 also accounts for the behavior and usage of the rescue inhaler unit by the primary patient. The behavior of the primary patient may refer to the number of rescue usage events and the frequency of the rescue usage events over a given time period. In one implementation, the given time period is at least one month. Accordingly, the clustering module 131 may not begin generating the aggregate data set until the one month has passed from the date at which the patient profile was initialized.

After accessing contextual data from the primary patient store, the clustering module 131 identifies 710 secondary patients with similar patient profiles (e.g., a similar frequency of rescue inhaler usage activity, demographic information, and medication data) to the primary patient. Depending on the primary patient, each factor of the demographic data may be weighted differently when identifying similar secondary patients. For example, the medication type may be weighted more heavily than the patient's gender, indicating that, in terms of their medication profiles, the medication type more heavily affects the similarity between two patients than their gender. In one implementation, the geographic distance between the location of the is weighted more heavily than other demographic data because users in the same locality are often exposed to the same environmental conditions. Users sensitive to triggers which rarely if ever occur in a geographical area may never exhibit symptoms of those triggers and therefore may lack the corresponding patient data to diagnose such triggers in the primary patient. Accordingly, users who are also sensitive to the same local triggers as the primary patient will manifest similar symptoms in their secondary patient data.

As described above, in some implementations, behavioral data describing the frequency with which a rescue usage event occurs may be characterized on a per day basis as a feature vector comprising integer values for each trigger recorded during that day. On days during which the trigger values fluctuated throughout the day, the feature vector may include an average of the different trigger values. In such implementations, the clustering module may weight individual trigger conditions more heavily than others. For example, if the wind speed trigger has already been determined to be an insignificant trigger to the primary patient, the clustering module 530 may assign it a lower weight than the remaining trigger conditions and revise the aggregate dataset to include secondary patients who were also determined to be insensitive to the wind speed trigger.

In some implementations, the clustering module 530 implements a nearest neighbor search to identify a group of secondary patients similar to the primary patient. The nearest neighbor search may identify a specific number of secondary patients, for example the k nearest neighbors, depending on the amount of patient data already recorded. If only a small amount of primary patient data has been recorded, for example two months' worth of data, the clustering module 530 may identify a larger set of nearest neighbors compared to if three years' worth of primary patient data had been recorded. Accordingly, in some implementations, the composition of the aggregate dataset may be continuously updated as the primary patient data store 510 receives current rescue usage event data 550. More specifically, as the primary patient data store 510 is updated with current rescue usage event data 550 and that data is received by the clustering module 530, the clustering module 530 may remove secondary patient data related to the secondary patients who are least similar to the primary patient to optimize the amount of computer memory required to store the aggregate database. As a result, the clustering module 530 may conduct a nearest neighbor search of the secondary store during each update of the primary patient data store 510. In implementations in which computer storage memory need not be optimized, the clustering module 530 may add the current rescue usage event data 550 to the aggregate dataset while maintaining all patient data already included in the aggregate dataset. Examples of k-nearest neighbor searches which may be implemented by the clustering module 530 include, but are not limited to, latent class analysis, a KD-tree nearest neighbor search, or an alternate search technique. In one implementation, the clustering module 530 identifies a set of the nearest neighbors from the secondary patient data store 520 based on the similarity of their demographic information, the trigger values during each day, and the trigger values recorded during rescue usage events. In one implementation, trigger values inputted to the model are scaled such that the mean is 0 and the standard deviation is 1 and are weighted according to a combination of expert domain knowledge. The weights assigned to the various triggers are extrapolated from asthma risk predictive models. The weights are verified by randomly perturbing a subset of the weights, running the model, and comparing the information gained or lost when those weights are randomized. Weights that result in a loss of information (i.e., fewer triggers identified at a set of confidence levels, controlled for false discovery rates) are up weighted.

After identifying a set of secondary patients to be included in the aggregate dataset, the clustering module 530 determines 715 and assigns a weight representing the similarity of each secondary patient to the primary patient. The clustering module 530 assigns weights based on the similarity of the secondary patients to the primary patient such that the most similar secondary patients are assigned the highest weights and the least similar patients are assigned the lowest weights. When assigning a weight to each secondary patient, the clustering module 530 assigns the weight to each feature vector associated with the secondary patient and the feature value for each trigger condition in each feature vector. For example, a secondary patient highly similar to the primary patient may be assigned a weight of 0.9. The secondary patient may be associated with 90 days' worth of feature vectors stored within the aggregate dataset. When determining the relative risk score, each trigger value for each of the 90 feature vectors may be converted to a weighted trigger value, based on the assigned weight of 0.

In contrast to the weights assigned to the secondary patients, "initial weight" assigned to the feature vectors of the primary patient data (e.g., weight of value 1) is greater than the weights assigned to the secondary patient data (e.g., weights in the range of 0 to less than 1) such that primary patient data has a greater impact on the trigger identification than any one secondary patient. In some implementations, the weights assigned to feature vectors of both the primary patient and each secondary patient are correlated with the count of rescue inhaler usage events for the primary patient within the aggregate dataset. For example, if 30 days' worth of primary patient data are included within the aggregate dataset and only one rescue usage event was detected, the primary patient data may not provide significant insight as to which triggers the primary patient is sensitive too compared to a very similar secondary patient with 30 days' of patient data included in the aggregate dataset and 10 detected rescue usage events. Accordingly, the clustering module 530 may decrease the weight assigned to the primary patient data and increase the weight assigned to the secondary patient data or maintain the weight assigned to the primary patient data and increase the weight assigned to the secondary patient data. The determination of the weights is further discussed in Section IV.C.1 with reference to training the model 560.

After identifying the set of nearest secondary patients and assigning a weight to each one, their associated feature vectors, and the clustering module 530 compiles the data to generate 720 an aggregate dataset describing contextual data from days during which primary patients and secondary patients have been in possession of a rescue usage inhaler. As described above, the clustering module may periodically update 725 the aggregate dataset based on newly received current contextual event data 550 stored within the primary patient data store 510.

In some implementations, the clustering module 530 may dynamically adjust the weights assigned to both the primary patient and the secondary patient as the composition of the aggregate dataset updates. When the primary patient data store 510 and receives current contextual event data, the clustering module 530 incorporates that data thereby increasing the amount of primary patient data in the aggregate dataset. As the amount of primary patient data in the aggregate dataset resultantly increases, the clustering module may dynamically increase the weight assigned to the primary patient's feature vectors and decrease the weights assigned to feature vectors of the secondary patient to further emphasize the primary patient data in the trigger analysis. In the implementations described above in which the secondary patient data is periodically removed from the aggregate data store, the clustering module 530 identifies and removes the secondary patient feature vectors assigned the lowest weights.

IV.B.2 Trigger Splitting Protocol

The aggregate dataset generated by the clustering module 530 is processed by the trigger splitting module 540 into a converted representation. Each trigger value of the aggregate dataset is replaced with a set of binary labels indicating whether or not the trigger was present, at various trigger values, during the day on which the feature vector was generated. For each trigger, the trigger splitting module identifies several similar triggers and bifurcates each similar trigger into a set of trigger conditions: one condition indicating that a feature was present on a given day and a second range indicating that the feature was not present on a given day. Any of the similar trigger values for which the trigger conditions is true area assigned a common label, for example a "1", and any similar trigger values for which the trigger condition is false are assigned a common label, for example a "0". As a result, each feature vector with a diverse array of feature values is processed into a an array of binary feature values. As described herein, a label of "1" is assigned to trigger values that are true under a trigger conditions and a label of "0" is assigned to trigger values that are false under a trigger condition. However, the trigger splitting module 540 may implement any set of binary labels consistent with the description of the trigger splitting module 540.

Certain triggers may only have a binary range of trigger values, for example gender. For such triggers, the trigger condition is determined by selecting one value of the binary range and if the trigger value is the value selected for the trigger condition, the trigger splitting module 540 assigns the trigger value a label of "1". If the trigger value is not the value selected for the trigger condition, the trigger splitting module 540 assigns the trigger value a label of "0". Continuing from the gender example, a feature vector may be associated with a female patient. The trigger condition determined by the trigger splitting module 540 may be one of the following: "Male?" or "Female?". If the trigger splitting module 540 selects "Female?" as the trigger condition, the trigger value for the female patient is assigned a label of "1." Alternatively, if the trigger splitting module 540 selects "Male?" as the trigger condition, the trigger value for the female patient is assigned a label of "0".

Other triggers may have a larger range of at least three values, for example temperature. For such triggers, the trigger splitting module may identify a set of similar trigger values within the range of trigger values. In one implementation, each value within the range of trigger values is included in the similar set of trigger values. For example, the temperature trigger has a range of trigger values including every integer between 0° C. and 100° C. and the trigger splitting module 540 includes each integer value in the set of similar trigger values (i.e., 0° C., 1° C., 2° C., 3° C. . . . 100° C.). In alternate implementations, the trigger splitting module 540 includes ranges of trigger values in the set of similar trigger values rather than individual trigger values (e.g., 0-20° C., 21-40° C., 41-60° C., 61-80° C., 81-100° C.). For each patient and feature vector, the trigger splitting module 540 compares the trigger value to each similar trigger value to determine which of the binary labels to assign to the similar trigger value. When a trigger value in a feature vector matches with a similar trigger value, the trigger splitting module 540 may assign a label of "1" and when the trigger value does not match, the trigger splitting module 540 may assign a label of "0".

Figure 8:
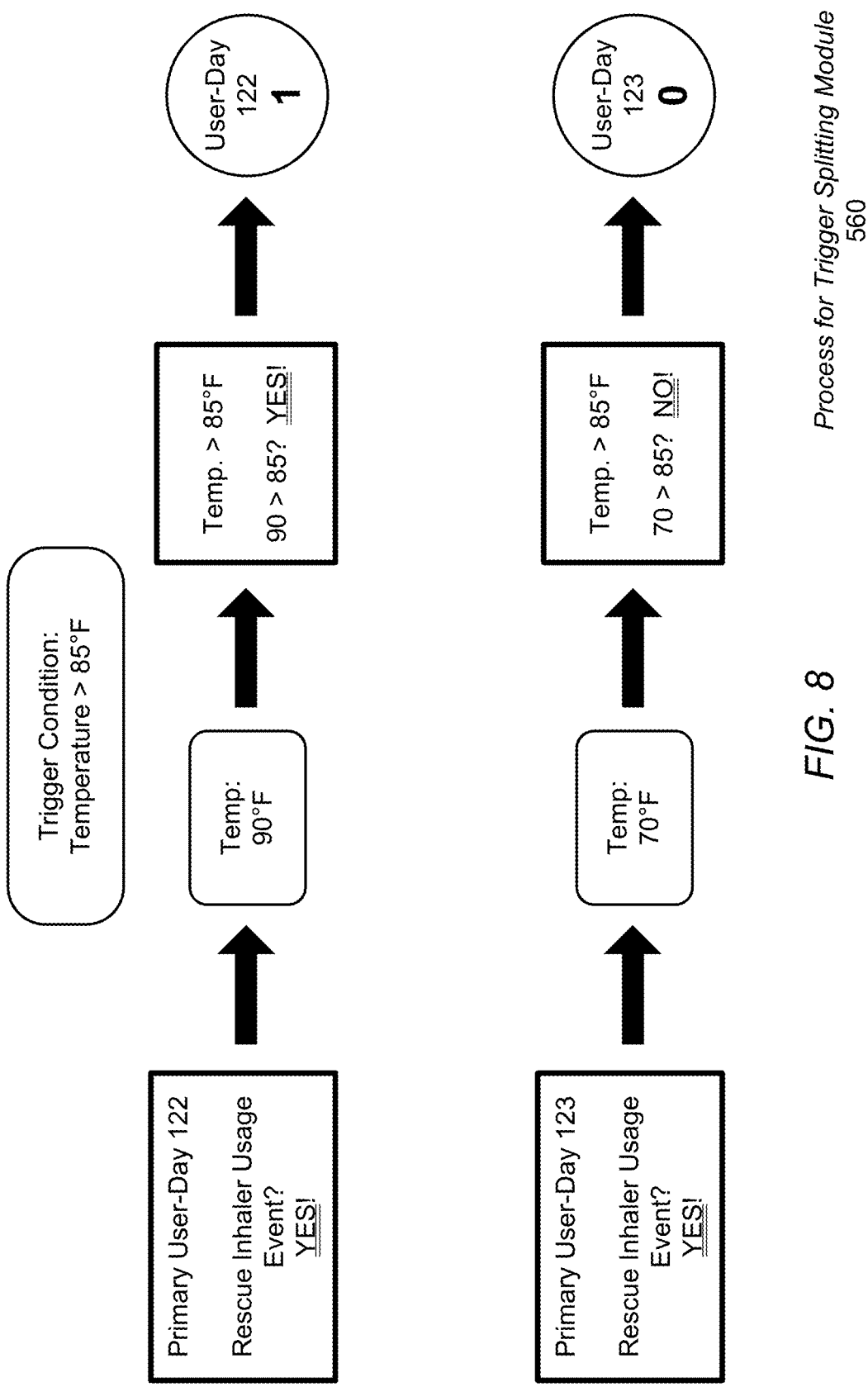
FIG. 8 is a diagram illustrating the method for assigning binary labels to a trigger, according to one embodiment.

FIG. 8 is a diagram illustrating the method for assigning binary labels to a similar trigger value for a trigger, according to one embodiment. FIG. 8 illustrate two example labels assigned to two similar trigger values for a common trigger condition. The trigger splitting module identifies two consecutive days during which the rescue inhaler unit detected a rescue usage inhaler event-primary user-day 122 and primary user-day 123. In the illustrated implementation, the trigger values for a temperature trigger are being evaluated and labeled. The feature vector describing the primary user-day 122 indicates that a temperature value of 90° F. was recorded on that day and the and the feature vector describing primary-user day 123 indicates that a temperature value of 70° F. was recorded on that day. The trigger splitting module 540 identifies, from the set of similar trigger values, the similar trigger value of 85° F. and generates a trigger condition of "Temperature above 85° F.?" which defines any day with a temperature value above the 85° F. as indicative that the trigger was present during that day. Accordingly, the trigger splitting module 540 assigns a label of "1" to the similar trigger value for primary user-day 122 because a temperature of 95° F. is greater than the threshold temperature of 85° F. The trigger splitting module 540 assigns a label of "0" to the similar trigger value for primary user-day 123 because a temperature of 70° F. is less than the threshold temperature of 85° F.

In an alternate implementation (not shown) the trigger condition may be defined as "Temperature below 85° F.?" based on the average temperature recorded on days during which a rescue usage event was detected. In such an implementation, the trigger splitting module 540 would instead assign a label of "0" to the temperature trigger value for the primary user-day 122 and a label "1" to the temperature trigger value for the primary user-day 123.

IV.B.3 Example Aggregate Dataset

After being processed by the trigger-splitting module 540, the aggregate dataset comprises a number of feature vectors of binary labels, which may for convenience be organized by day and by patient. FIG. 9 is a diagram illustrating an example visualization of the aggregate dataset. As illustrated, the aggregate dataset is a table of data wherein each row represents a feature vector for a specific day and a specific patient. The illustrated section of the aggregate dataset describes patient data recorded on May 25$^{th}$ for patients 1 (the primary patient), 2.a, 2.b, 2.c, 2.d (the secondary patients). The aggregate dataset comprises a larger number of days' worth of data and a large population of secondary patient such that the FIG. 9 only illustrates a small sample of the data stored in the aggregate dataset. As described above, each secondary patient is assigned a weight indicating their level of similarity to the primary patient. In some implementations, the aggregate dataset may be organized by ranking the secondary patients based on the weights assigned to them, for example ascending or descending order.

The horizontal labels of the table includes trigger information, including the triggers (labeled at the top of the table in FIG. 9), and example binary triggers and the associated value/condition assigned to that binary trigger (labeled at the bottom of the table in FIG. 9). As described, above triggers include demographic data, for example gender and age, clinical data, for example medication amount and adherence, and contextual data, for example home location, temperature, humidity, station pressure, wind speed, concentration of nitrogen dioxide, concentration of ozone, concentration of sulfur dioxide, and measurements of particulate matter in the air. Implementations of the data analysis model 131 may expand the amount of triggers analyzed to include additional data, for example clinical assessments of patients, patient symptoms, and the results of an Asthma Control test. The trigger conditions identified in the above descriptions are not meant to be limiting, but rather exemplary of the kinds of conditions which the data analysis module 131 considers when evaluating trigger conditions. Trigger conditions assigned to trigger values associated with a non-binary range of values are represented as a comparison to a threshold value, for example "greater than" or "less than," whereas trigger conditions assigned to trigger values associated with a binary range of values are described as "equal to one of the binary values."

For simplicity, FIG. 9 illustrates a label assigned to only a single similar trigger value, however in practice the general aggregate dataset may comprise multiple labels each assigned based on the trigger conditions for a different similar trigger value. Returning to the temperature example described in Section IV.A, the aggregate dataset would include a label assigned to each similar value derived from the range of trigger values (i.e., a binary label assigned to the similar trigger values 0° C., 1° C., 2° C., 3° C. . . . 100° C.).

The relative weights assigned to the secondary patient are based on the levels of similarity to the triggers recorded for the primary patient. Referring back to FIG. 9, on May 25$^{th}$, patient 2.a experienced the same trigger conditions as the primary patient 1 for all triggers except for the measurement of ozone. Patient 2.b experienced the same trigger conditions as the primary patient 1 for all triggers with the exception of 6-gender, home location, temperature, measurement of nitrogen dioxide, and measurements of particulate matter 2.5 micrometers or less and particulate matter 10 micrometers or less. Patient 2.c and 2.d recorded different trigger conditions for 10 and 15 triggers, respectively. According the highest weight of 0.9 is assigned to secondary patient 2.a most similar to the primary patient and the lowest weight of 0.1 is assigned to the secondary patient 2.d least similar to the primary patient.

IV.C Relative Risk Determination

For each trigger included within the aggregate dataset, the model 560 determines an aggregate dataset based on the contextual data for each patient within the aggregate dataset. In some implementations, the model 560 is a mathematical function or another more complex logical structure. The model 560 determines a baseline threshold describing a number of rescue usage events per day which would constitute a cause for alarm. For example, if the baseline threshold is determined to be two rescue usage events, days in which three or more rescue usage events occurred would be flagged as exacerbation days. The model 560 analyzes the aggregate dataset to group each exacerbation day into a group of days in which a trigger was present and a group of days during which the trigger was not present (based on the trigger conditions described above). The model 560 performs this separation individually for each trigger stored within aggregate dataset. For each of the separated groups, the model 560 determines a relative exacerbation based on the ratio of exacerbation days in the group to the total number of days in the aggregate dataset and a relative risk by determining the change in relative exacerbations between the two groups. In some implementations, the model is sensitive to type I errors (i.e., false positives), but desensitized to type II errors (i.e., false negatives). In alternate implementations, the model may be sensitized to both type I and type II errors.

IV.C.1 Model Training

When inputting the trigger values of a trigger into the model 560, the model 560 receives the weights describing the level of similarity between each secondary patient and the primary patient. In some implementations, the weights are received from an authorized provider. In alternate implementations, the weights may be determined by training the model 560. To compute and assign the weights to each feature vector associated with the secondary patient data, the model 560 is trained using a training set an aggregate dataset of contextual data comprising contextual data for a test primary patient and a set of secondary patients. The training data set comprises one a set of known labels for the trigger identification (the labels indicating whether the patient was sensitive to each binary trigger) for a test primary patient and an aggregate dataset of primary and secondary patient data which may be used to determine the known labels. In some implementations, multiple training data sets may be implemented, each with their own set of known labels for the trigger identifications of a test primary and aggregate dataset. The known labels for the trigger identifications of the primary patient may be determined based on manual sensitivity tests performed by a physician on the test patient to physically test their responses to the triggers. For the simplicity of the training data set, in one implementation, labels assigned to the triggers are binary labels indicating "sensitive" or "insensitive."

In implementations employing a training data set, the model 560 may be trained by determining weights for each secondary patient feature vector that best represent the relationship between trigger values of each feature vector and the trigger identification labels of the test candidate. The model 560 is trained using a function or another more complex logical structure. In one embodiment, the model 560 is trained using a machine learning technique, examples of which include but are not limited to linear, logistic, and other forms of regression (e.g., elastic net), decision trees (e.g., random forest, gradient boosting), support vector machines, classifiers (e.g. Naïve Bayes classifier), and fuzzy matching.

Once the weight values are known and assigned to each secondary patient or feature vector, the model 560 may be used by receiving the weights and the function specified by the model, and inputting feature values to generate a risk score. In one implementation, the weights determined during the training of the model may be assigned sequentially (i.e., in order of the most similar secondary patient to the least secondary patient), such that when implemented the sequentially corresponding secondary users of the same current aggregate dataset are assigned the same weights. For example, the weight determined for kth secondary user of the training dataset is assigned to the kth user of the aggregate dataset being presently analyzed.

IV.C.2 Threshold Determination

As introduced above, baseline thresholds are used both in training the model and the risk score calculation. The model 560 calculates the baseline threshold based on the total number of usage events over a specific prior time period preceding either the current day during which the risk is being calculated (for either labeling during the training or during model use), or more generally during a time period preceding the time of a current/most recent rescue usage event.

In one example, the time period is a range bounded by the current day and seven days prior, In one example, the time period is a range bounded by the current day and seven days prior, exclusive (so, excluding the current day's data from consideration), however other time periods may be used. If there are not seven days' worth of data accumulated, for example due to a patient profile having recently been created or usage events not having been tracked during this time window, the baseline may instead be calculated based on the number of days for which data is available.

In one embodiment, the baseline risk threshold is set as a fraction (percentage) of the total number of usage events over the specified period, however in other embodiments, other functions of the total number of usage events may be used to determine the threshold. First, the total number of rescue usage events from a preceding seven day period may be summed and recorded, for example for a total of 30 events. Second the baseline threshold is determined as the number of events equal to a fraction of the total, for example 5% of the total or 1.5 events. To label a day as an exacerbation day, the model 560 assigns a label if the number of rescue inhaler usage events in a given day is greater than the threshold, for example greater than 5% of the 30 events tallied over the last seven days. Otherwise, the day is assigned an alternate label indicating that the day did not qualify as an exacerbation day.

The setting of the threshold based on a fraction of the prior period's events, as opposed to a fixed number of events, allows for greater flexibility and variability in tailoring the threshold to the patient's or region's specific disease or regional state. For example, if the patient's rescue inhaler usage is elevated over a number of days, then having the threshold be dynamic in this manner allows better identification of whether the parameters are (or are not) exacerbating the patient's condition. In one embodiment, the baseline risk threshold is set to 5% rather than some higher threshold such as 14% (representing a 1 day average out of a 7 day history) to account for right tailed usage patterns with asymmetric distribution due to frequent 0's and to ensure high risk categorizations of days with usage events greater than a median day yet below the 7-day average.

IV.D Sensitivity Analysis for Triggers

To determine whether the relative risk score for a trigger indicates that a primary patient is sensitive to the trigger, the sensitivity module 570 determines the significance and confidence of the relative risk score based on a comparison to one or more confidence intervals using statistical analysis techniques, for example a weighted sequential probability ratio test (SPRT). The sensitivity analysis module may implement any other analysis technique, including those used by the US Food and Drug Administration to monitor drugs for potential recalls due to adverse side effects not seen during clinical trials.

After determining that the number of number of exacerbation days exceeds when the trigger was present exceeds the baseline threshold of rescue usage events from a previous interval, the sensitivity module 570 may implement statistical analysis techniques to determine if the increase in rescue usage is a result of the trigger condition. In one implementation, the sensitivity module 570 uses, as inputs to a statistical model, for each a weighted normalization term based on a distance metric describing similarity the primary patient to each secondary patient, the relative risk score for the trigger, the baseline threshold, and the number of exacerbation days during which the trigger was present to determine a Weighted Log Likelihood Ratio (WLLR). The WLLR may be an aggregate function of the weighted normalization factors for each secondary patient in the aggregate dataset.

The distance metric describes a Euclidean distance between trigger values associated with the primary patient and the secondary patient. Similar to the description above in Section IV.C regarding weights assigned to secondary patient data, the weighted normalization term is inversely related to the distance metric, such that the closer the distance between the primary patient and the secondary patient, the higher the weight assigned.

The WLLR is then compared against two boundary conditions, or confidence intervals which are functions of the significance, or type I error rate, and the power, or type II error rate. When the WLLR violates the lower bound confidence interval, the sensitivity module 570 concludes that the relative risk score for the trigger does not indicate that the patient is sensitive to the trigger. When the WLLR violates the upper bound confidence interval, the sensitivity module 570 concludes that the relative risk score for the trigger does indicate that the patient sensitive to the trigger.

The sensitivity module 570 may compare the WLLR to several sets of confidence intervals and determine a level of confidence in the sensitivity determination for the trigger. For example, if the WLLR exceeds an upper bound confidence interval associated with a low confidence level, but violates a lower bound confidence interval associated with a high confidence level, the sensitivity scoring module 570 may abstain from determining the primary patient's sensitivity to the trigger until more data is available. However, a different WLLR which exceeded the upper bound confidence interval associated with the higher confidence level may be sufficient to identify the primary patient's sensitivity to the trigger.

Figure 10:
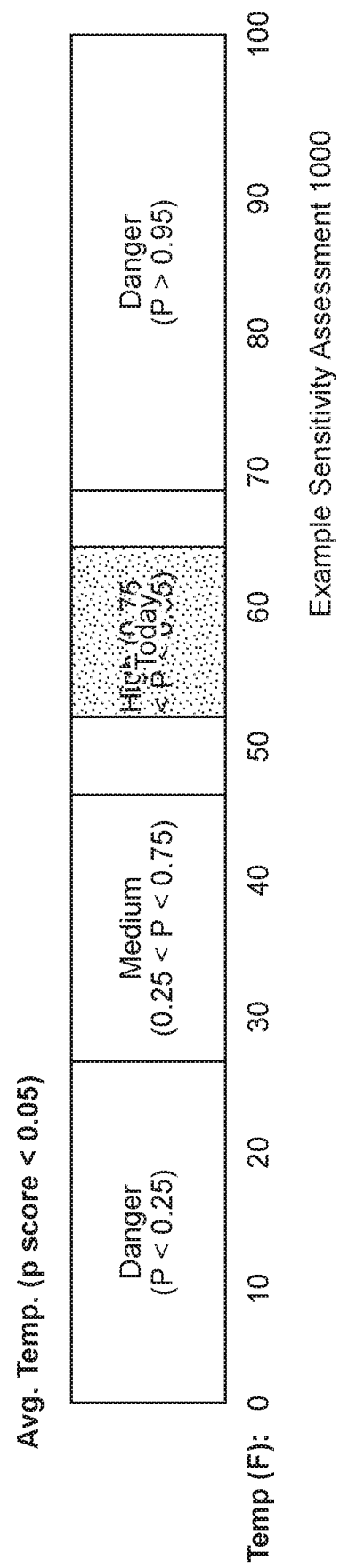
FIG. 10 is a diagram illustrating an exemplary sensitivity assessment for a trigger, according to one embodiment.

In some implementations, the sensitivity scoring module 570 may also be implemented to determine the level of risk an individual trigger poses to a patient on a given day. Once a patient has been identified as sensitive, insensitive, a degree of sensitive to a trigger, the sensitivity module 570 may categorize ranges of trigger values with levels of sensitivity. FIG. 10 is a diagram illustrating an exemplary sensitivity assessment for a trigger, according to one embodiment. As illustrated in FIG. 10, ranges of trigger values on either extreme may be designated as indicative of a high risk, while ranges near the middle may be designed as medium or low risk depending on the results of the SPRT discussed above.

IV.E Trigger Identification Notifications

The notification module 580 generates a trigger identification notification including any one or more of: the identified trigger, remaining unidentified triggers, information characterizing the identified trigger, suggestions and recommendations for addressing the identified trigger or avoiding rescue usage events.

Figure 11:
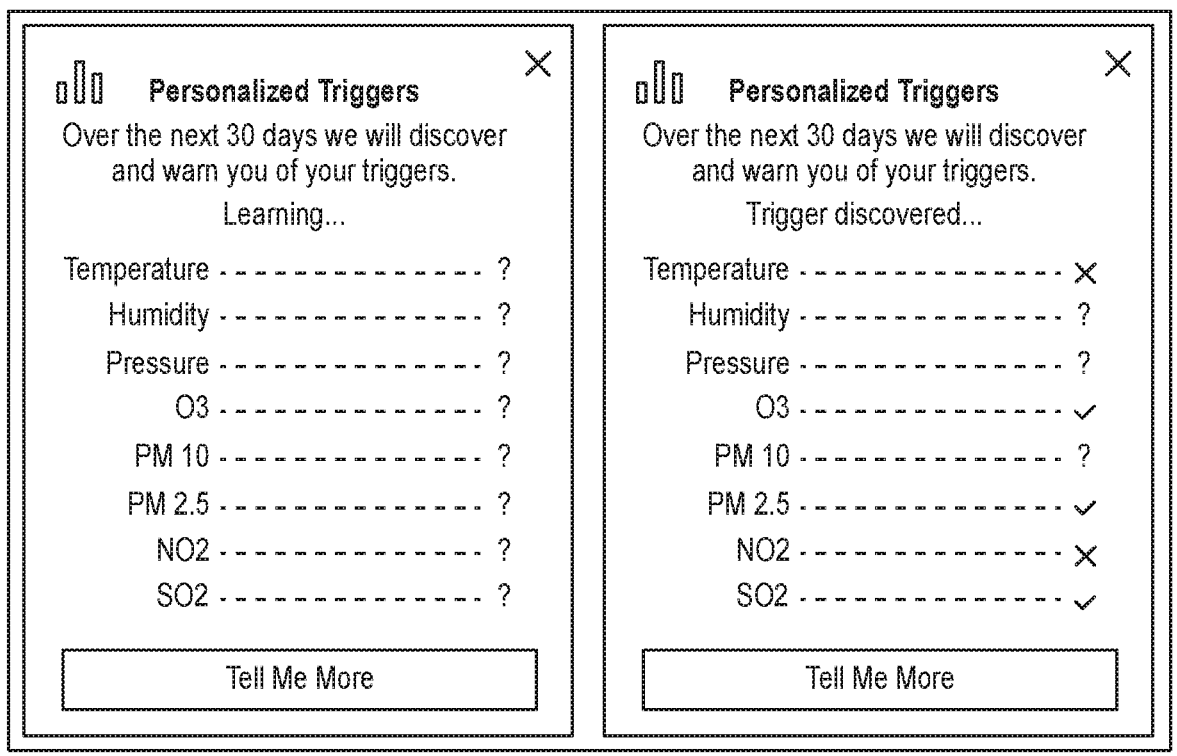
FIG. 11-12 shows example cards displayed to a client in response to identifying a trigger, according to one embodiment.
Figure 12:
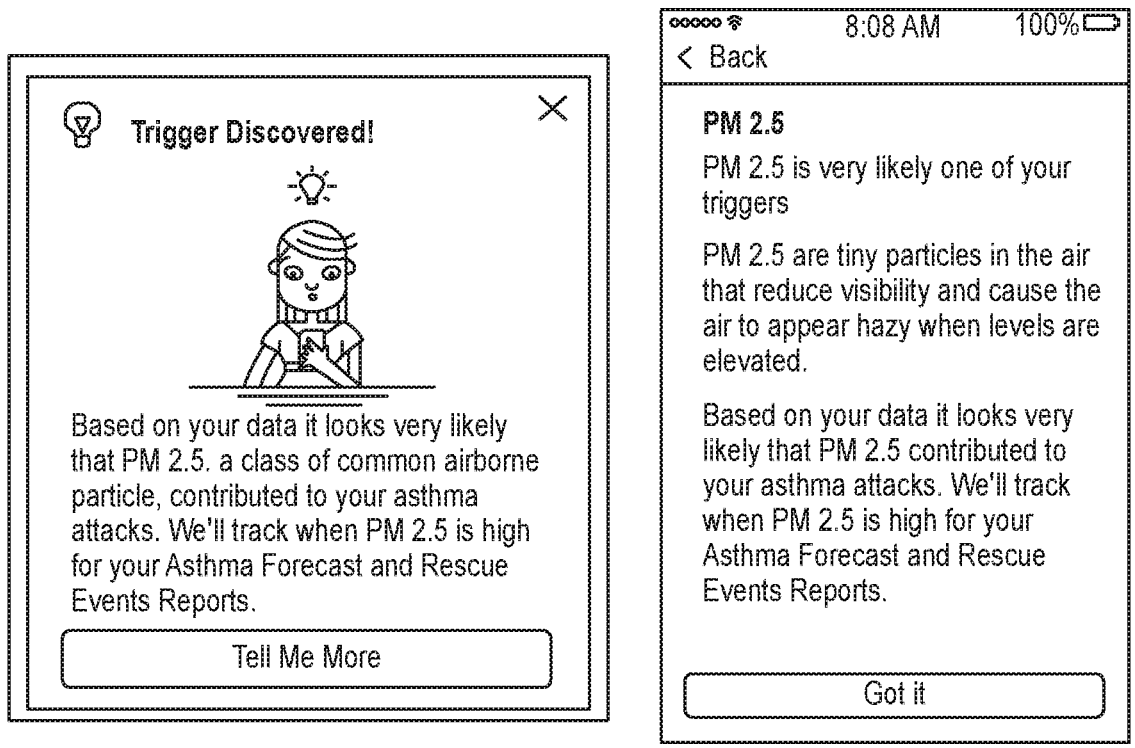

FIGS. 11-12 show example cards displayed to a patient in response to the identification of a trigger, according to one embodiment. FIG. 11 describes an interface presenting the progress that the data analysis module 131 has made in identifying a set of triggers for a primary patient and the severity of each trigger. In the illustrated implementation, triggers which have been identified are presented with a red "X" or a green check, where the X represents triggers to which the patient is not sensitive and the check represents triggers to which the patient is sensitive. The interface may also include a metric describing the confidence in the identification of the trigger, for example the amount row of dots. In FIG. 11, the row of colored dots may be assigned a color representing the sensitivity of the patient, for example the color red indicates that the patient is not sensitive and the color green indicates that patient is sensitive. As the sensitivity module 570 increases the confidence level with which it identifies the trigger, the confidence metric, or row of dots, may be colored in further. Before the confidence in each trigger exceeds a threshold confidence, the trigger may be assigned an inconclusive icon, for example a question mark, indicating that the trigger has not yet been identified with a threshold level of confidence. Because of the dynamically changing confidence metric, the notification module 580 may alert the user whenever progress is made, even in small frequent changes.

FIG. 12 describes interfaces presented to a patient in response to a trigger being identified. Notifications may be sent out in response to the identifications of triggers which the primary patient is sensitive to and insensitive to. The notifications include a description of the identified trigger, for example "PM2.5 are tiny particles in the air that reduce visibility and cause the air to appear hazy when levels are elevated." In some implementations, the trigger notifications may describe medication regimens which the primary patient may use in the presence of a trigger condition or lifestyle recommendations for the patient to reduce their sensitivity to the trigger. In some implementations, the risk notification module 580 delivers a notification to a user when the application is closed or when the client device is not being used. The notification may be stored on the client device until the primary patient has an opportunity to review the data.

Figure 13:
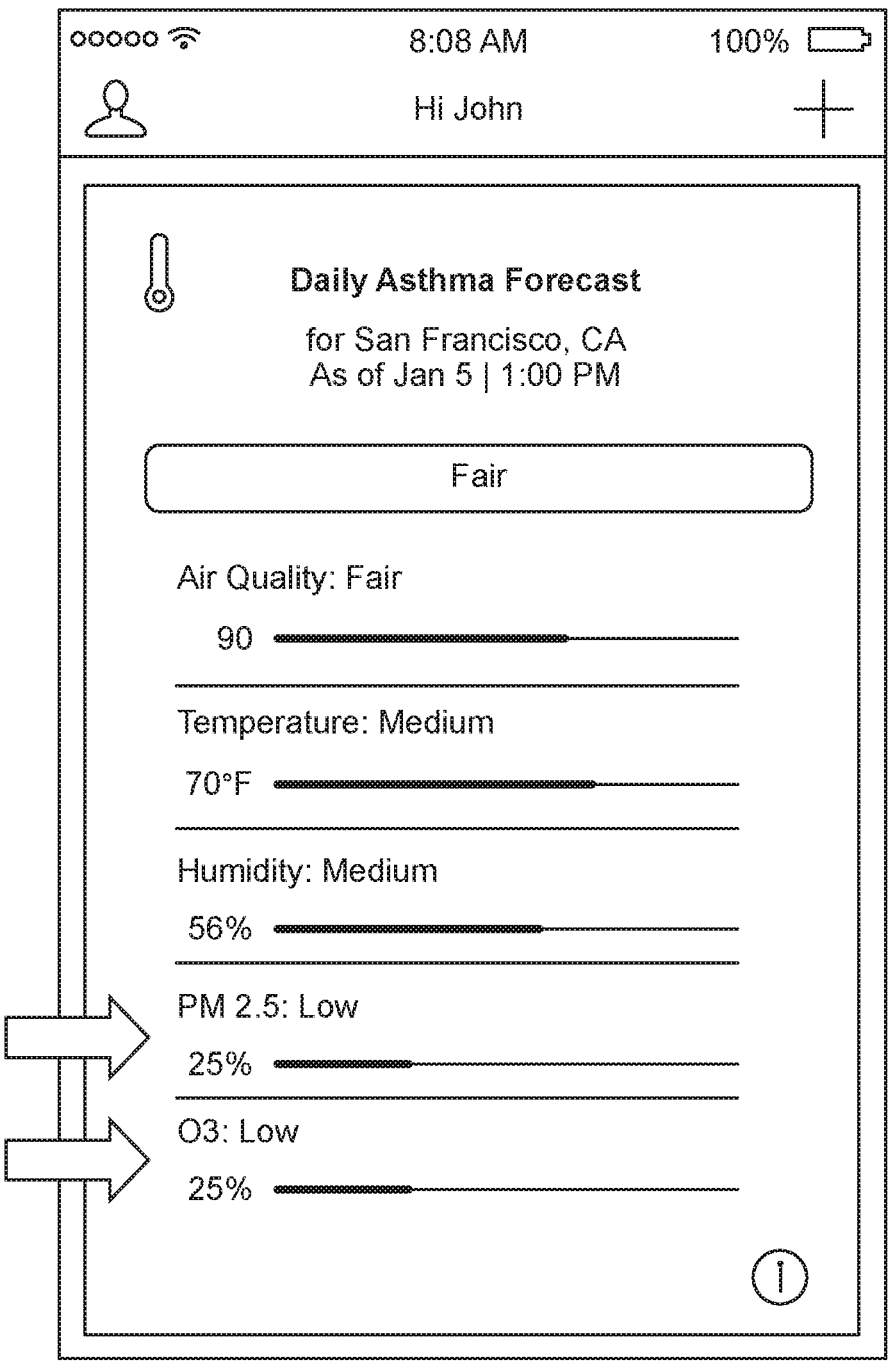
FIG. 13 shows an example card displayed to a client describing their potential risk of triggering event, according to one embodiment.

FIG. 13 shows an example card displayed to a client describing their potential risk of triggering event, according to one embodiment. FIG. 13 illustrates an interface presenting a daily forecast of the potential a user will experience a rescue usage event given the current contextual conditions of the primary patient and their known triggers. For example, the primary patient viewing the interface, John, may be sensitive to two triggers: the measurement of particulate matter 2.5 micrometers or less and the measurement of ozone in the air. When those two conditions are measured to be low while the other conditions are held constant, the forecast may describe the conditions as fair. However, if the measurements of either trigger were to increase, the forecast may be updated to describe the conditions as poor. When the forecast recognizes poor or unfavorable conditions, the notification module 580 may deliver a notification to the primary patient informing them and including instructions for how best to handle the change in conditions while maintaining their health.

The trigger notification may also be delivered in many other situations which depending upon the implementations, for example in response to a rescue usage event, or may be sent to the client device according to some other mechanism. The notification module 580 may also generate risk notifications. For example, if a patient's or region's current contextual conditions worsen due to changes in patient parameters or environmental condition parameters an updated risk notification may be delivered to the user based on one or more previously identified triggers. Risk notifications may also be delivered at a user's request, for example due to a verbal request for local asthma conditions from a third party device (e.g., Google Home™ or Amazon Alexa™) or via other platforms.

Generally, trigger and risk notifications are delivered through the client device 110, however, in other embodiments, in the event of improved or worsened conditions, risk notifications may be delivered as an SMS notification, an email notification from an embeddable widget with local asthma conditions, or notifications from various IFTTT applets (https://ifttt.com/).

V. Benefits

The trigger identification notifications provided to patient 111, providers 112, and users more generally convey many benefits. Patients are informed of their causes of a respiratory related event in real time or near real time as rescue usage events occur and can take actions to address or avoid those triggers, for example by adding or altering their prescribed medication regimen (such as an adjustment of dosage or the introduction of antibiotics or systemic corticosteroids) or by avoiding geographic areas with adverse condition (e.g., air pollution concentrations). Because event data is automatically reported to the application server 130 without the need for patient input, the accuracy and quality of the event data used to identify triggers is improved relative to manually-collected data by a health care provider 112 or other entity, and thus accuracy of the conclusion for the risk for asthma rescue events is also improved.

Additionally, notifications provided by the application server 130 provide patients with additional information about the identified trigger, solutions to address the trigger, and their personal risk of rescue usage events on a given day based on that trigger. Notifications further encourage the user to play an active role in the management of their respiratory disease, for example asthma or COPD.

Information describing a trigger analysis for a patient based on their contextual data allows patients suffering from respiratory diseases to make informed lifestyle choices regarding different geographical regions. For example, when searching for real estate, the ability to eliminate geographic regions with a high risk of one or more triggers allows a patients to make informed decisions to improve their health. Similarly, when traveling, prior knowledge of a risk for region allows patients to prepare the necessary precautions. As a result, a trigger analysis based on contextual data provides patients with anticipatory knowledge necessary for them to reduce their risk of respiratory events wherever their location may be.

VI. Additional Considerations

Although the discussion above focuses on asthma, all systems and processes described herein are equally applicable to chronic obstructive pulmonary disease (COPD) and chronic respiratory disease (CRD) generally, and consequently can also be used to assist in treatment of COPD and CRD, as well as asthma.

It is to be understood that the figures and descriptions of the present disclosure have been simplified to illustrate elements that are relevant for a clear understanding of the present disclosure, while eliminating, for the purpose of clarity, many other elements found in a typical system. Those of ordinary skill in the art may recognize that other elements and/or steps are desirable and/or required in implementing the present disclosure. However, because such elements and steps are well known in the art, and because they do not facilitate a better understanding of the present disclosure, a discussion of such elements and steps is not provided herein. The disclosure herein is directed to all such variations and modifications to such elements and methods known to those skilled in the art.

Some portions of above description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

While particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A method for identifying triggers of rescue inhaler usage for a patient, the method comprising:
receiving, from a medicament device sensor removably attached to a rescue inhaler unit and configured to monitor medicament usage of the rescue inhaler unit, a plurality of signals, wherein each signal of the plurality of signals describes a rescue inhaler usage event recorded by the medicament device sensor when the rescue inhaler unit dispense a rescue medication to the patient;
accessing, from one or more remote servers, measurements of one or more environmental triggers of a rescue medication event recorded during each rescue inhaler usage event described in the plurality of signals;
encoding a plurality of feature vectors, wherein each feature vector of the plurality of feature vectors corresponds to a rescue inhaler usage event described in the plurality of signals and is encoded with patient data for the patient and a value assigned to each of the one or more environmental triggers based on the measurement of the environmental trigger recorded during the rescue inhaler usage event, wherein
the value for each of the one or more environmental triggers describes whether a trigger condition for the environmental trigger was present when the rescue inhaler usage event was detected, the trigger condition representing a subset of measurements for the environmental trigger;
inputting the plurality of feature vectors encoded with patient data for the patient into a function trained, for each trigger condition, to:
categorize the plurality of feature vectors into a first subset of feature vectors where the trigger condition is present and a second subset where the trigger condition is not present; and
determine, for the patient, a relative risk score for the trigger condition based on a count of feature vectors in the first subset relative to a count of feature vectors in the second subset;
for each trigger condition,
determining a sensitivity of the patient to the trigger condition wherein determining the sensitivity of the patient comprises:
determining, by a statistical model, a weighted normalization term based on a similarity between the patient and each secondary user of a plurality of secondary users in an aggregate dataset, the relative risk score for the trigger condition, and a number of days during which the trigger event was present and;
comparing the weighted normalization term against a set of confidence intervals to determine whether the relative risk score for the trigger indicates that the patient is sensitive to the trigger; and
generating, for presentation to the patient, a notification describing the sensitivity of the patient to the trigger condition and suggestions for preventing rescue inhaler usage events when the trigger condition is satisfied.

2. The method of claim 1, further comprising:
at periodic intervals,
determining, for the patient, a relative risk score for the trigger condition based on feature vectors encoded with patient data recorded during each interval;
inputting the relative risk score into the statistical model; and
identifying the patient as sensitive to the corresponding trigger.

3. The method of claim 1, wherein patient data for the patient further comprises demographic information comprising one or more of the following:
an age of the patient;
a gender of the patient;
a medication type taken by the patient; and
a dosage for the medication type.

4. The method of claim 1, wherein patient data for the patient further comprises demographic information comprising one or more of the following:
an adherence metric for the patient, wherein the adherence metric compares a frequency per day with which the patient uses a controller medication to a frequency with which the patient is instructed to take the controller medication.

5. The method of claim 1, wherein the patient data for the patient further comprises demographic information comprising one or more of the following:
a behavior of the patient over a first month of using the rescue inhaler unit, the behavior describing the count of rescue inhaler usage events occurring over time period and a frequency at which rescue usage events occurred during the time period.

6. The method of claim 1, wherein an environmental trigger describes a threshold indicating one or more of the following:
a presence of a measurable quantity indicative of increased usage of the rescue medication; and
an absence of a measurable quantity indicative of decreased usage of the rescue medication.

7. The method of claim 6, wherein the measurable quantity includes one or more of the following:
at least one air pollutant condition, comprising:
ozone molecules ($O_3$);
nitrogen dioxide molecules ($NO_2$);
sulfur dioxide molecules ($SO_2$);
particulate matter, 2.5 micrometers or less ($PM_{2.5}$);
particulate matter, 10 micrometer or less ($PM_{10}$); and
air quality index (AQI).

8. The method of claim 6, wherein the measurable quantity includes one or more of the following:
at least one weather condition, comprising:
temperature;
humidity;
wind speed;
station pressure; and
visibility.

9. The method of claim 1, wherein the plurality of feature vectors encoded with patient data for the patient are further encoded with additional data comprising:
demographic information for a plurality of secondary patients;
a plurality of periods during which each secondary patient of the plurality of secondary patients used a client device, an attachment associated with a rescue inhaler unit, or the rescue inhaler unit, data for each period of the plurality of periods comprising a set of environmental triggers and a value of each environmental trigger; and a history of rescue inhaler usage events for each secondary patient.

10. The method of claim 1, further comprising:
assigning a first weight to values of environmental triggers encoded for the patient;
assigning a second weight to values of environmental triggers encoded for each secondary patient of the plurality; and
inputting the first and second weights into the function to determine the relative risk score.

11. The method of claim 10, wherein the first weight is correlated with a count of rescue inhaler usage events for the patient encoded in the plurality of feature vectors encoded with patient data for the patient.

12. The method of claim 10, wherein the second weights are correlated with a similarity of secondary patients to the patient.

13. The method of claim 10, further comprising:
determining the first weight and the second weight based on the count of rescue inhaler usage events encoded in the plurality of feature vectors; and
inputting the first and second weights into the function to determine the relative risk score for the patient.

14. The method of claim 10, further comprising:
for each secondary patient of the plurality of secondary patients, determining a similarity measurement between the secondary patient and the patient based on a closeness of demographic information and values for environmental triggers encoded for the patient and the secondary patient;
ranking the plurality of secondary patients based on the determined similarity measurements; and
adjusting the second weight assigned to each secondary patient of the plurality based on the ranking such that a higher ranked secondary patient is assigned a greater second weight than a lower ranked secondary patient.

15. The method of claim 10, wherein each secondary patient of the plurality of secondary patients is selected using latent class analysis.

16. The method of claim 10, wherein each secondary patient of the plurality of secondary patients is selected using a nearest neighbor analysis.

17. The method of claim 1, further comprising:
for each environmental trigger of the one or more environmental triggers, identifying a set of binary conditions each representing a range of possible values for the environmental trigger;
for each feature vector of the plurality of feature vectors, assigning a label to each trigger value identifying which binary condition of the set of binary conditions is satisfied by the trigger value.

18. The method of claim 1, wherein determining the relative risk score for the patient further comprises:
for each trigger condition,
identifying a first plurality of days where a rescue usage event occurred and the trigger condition was met;
identifying a second plurality of days where a rescue usage event occurred and the trigger condition was not met; and
comparing the first plurality of days and the second plurality of days to determine the relative risk score.

19. The method of claim 1, wherein determining the sensitivity of the patient to trigger condition further comprises:
comparing the relative risk score for the trigger condition to a confidence interval using a lookup table; and
determining that the patient is sensitive to the trigger condition based on the comparison.

20. The method of claim 1, wherein the sensitivity of the patient to the trigger condition is based on a combination of two or more trigger conditions.

21. The method of claim 1, wherein the sensitivity of the patient to the trigger condition is updated using a sequential probability ratio test.

22. The method of claim 1, wherein the notification describing the sensitivity of the patient to the trigger condition comprises one or more of the following:
the environmental trigger;
the trigger condition for the environmental trigger; and
a recommendation regarding how to prevent future rescue inhaler usage events based on the environmental trigger.

23. A non-transitory computer readable storage medium comprising computer program instructions that when executed by a computer processor cause the processor to:
receive, from a medicament device sensor removably attached to a rescue inhaler unit and configured to monitor medicament usage of the rescue inhaler unit, a plurality of signals, wherein each signal of the plurality of signals describes a rescue inhaler usage event recorded by the medicament device sensor when the rescue inhaler unit dispense a rescue medication to the patient;
access, from one or more remote servers, measurements of one or more environmental triggers of a rescue medication event recorded during each rescue inhaler usage event described in the plurality of signals;
encode a plurality of feature vectors, wherein each feature vector of the plurality of feature vectors corresponds to a rescue inhaler usage event described in the plurality of signals and is encoded with patient data for the patient and a value assigned to each of the one or more environmental triggers based on the measurement of the environmental trigger recorded during the rescue inhaler usage event, wherein the value for each of the one or more environmental triggers describes whether a trigger condition for the environmental trigger was present when the rescue inhaler usage event was detected, the trigger condition representing a subset of measurements for the environmental trigger;
input the plurality of feature vectors encoded with patient data for the patient into a function trained, for each trigger condition, to:
categorize the plurality of feature vectors into a first subset of feature vectors where the trigger condition is present and a second subset where the trigger condition is not present; and
determine, for the patient, a relative risk score for the trigger condition based on a count of feature vectors in the first subset relative to a count of feature vectors in the second subset;
for each trigger condition,
determine a sensitivity of the patient to the trigger, wherein instructions for determining the sensitivity of the patient to the trigger condition cause the processor to:
determine, by a statistical model, a weighted normalization term based on a similarity between the patient and each secondary user of a plurality of secondary users in an aggregate dataset, the relative risk score for the trigger condition, and a number of days during which the trigger event was present and;

compare the weighted normalization term against a set of confidence intervals to determine whether the relative risk score for the trigger indicates that the patient is sensitive to the trigger; and generate, for presentation to the patient, a notification describing the sensitivity of the patient to the trigger condition and suggestions for preventing rescue inhaler usage events when the trigger condition is satisfied.

* * * * *